(12) United States Patent
Puchhammer et al.

(10) Patent No.: US 8,100,986 B2
(45) Date of Patent: Jan. 24, 2012

(54) PROSTHETIC FINGER

(75) Inventors: Gregor Puchhammer, Vienna (AT); Martin Haslinger, Weiten (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 28 days.

(21) Appl. No.: 12/525,367

(22) PCT Filed: Jan. 31, 2008

(86) PCT No.: PCT/EP2008/000779
§ 371 (c)(1),
(2), (4) Date: Mar. 18, 2010

(87) PCT Pub. No.: WO2008/092695
PCT Pub. Date: Aug. 7, 2008

(65) Prior Publication Data
US 2010/0191343 A1 Jul. 29, 2010

(30) Foreign Application Priority Data
Feb. 1, 2007 (DE) .......................... 10 2007 005 858

(51) Int. Cl.
*A61F 2/54* (2006.01)

(52) U.S. Cl. ........................................................ 623/64
(58) Field of Classification Search .................... 623/57, 623/64, 65
See application file for complete search history.

(56) References Cited

U.S. PATENT DOCUMENTS
6,260,902 B1 * 7/2001 Synnelius ...................... 294/106
2006/0266146 A1 * 11/2006 Waide ......................... 74/424.92

FOREIGN PATENT DOCUMENTS
EP           1 457 294           9/2004

* cited by examiner

*Primary Examiner* — Bruce E Snow
(74) *Attorney, Agent, or Firm* — Whitham Curtis Christofferson & Cook, PC

(57) ABSTRACT

The invention relates to a prosthetic finger (1) with a proximal member (10), a medial member (20) and a distal member (30) that are mounted pivotably on one another, and with a motor (40) which is arranged in the prosthetic finger (1) and which, via a gear mechanism, rotates the medial member (20) relative to the proximal member (10), said medial member (20) accommodating a longitudinally movable balance arm (90) which is connected via levers (91, 93) to the proximal member (10) and to the distal member (30).

32 Claims, 23 Drawing Sheets

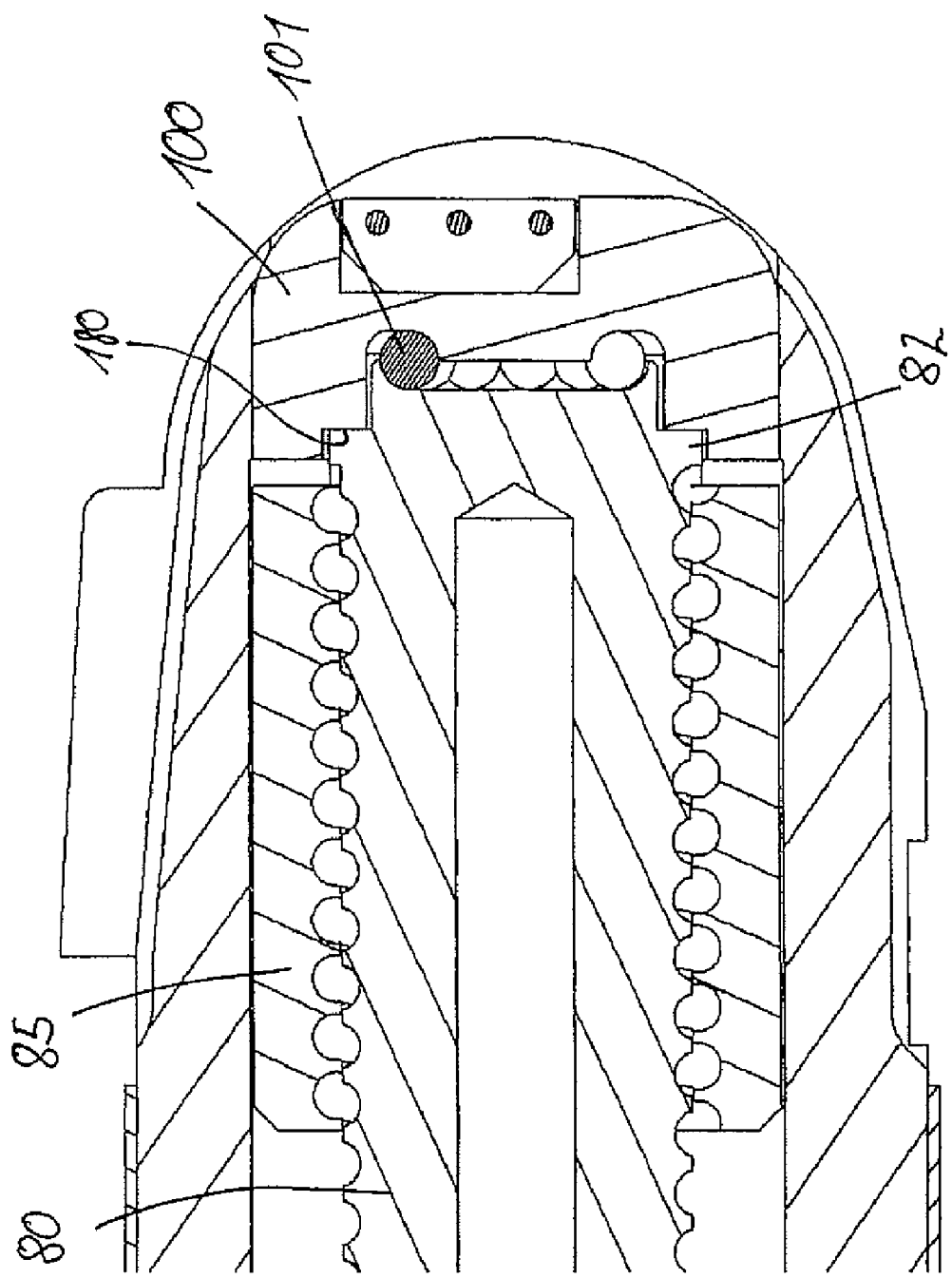

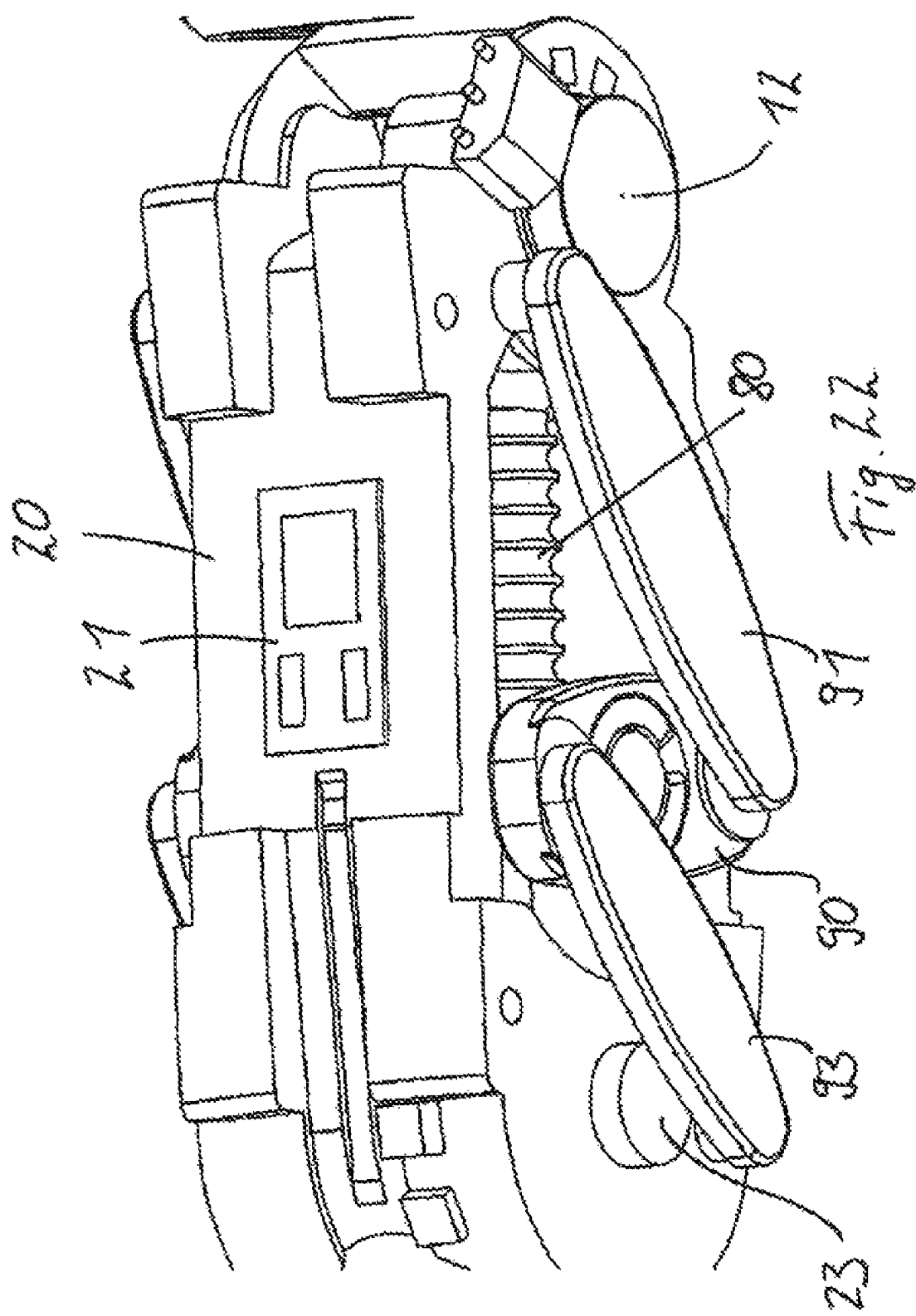

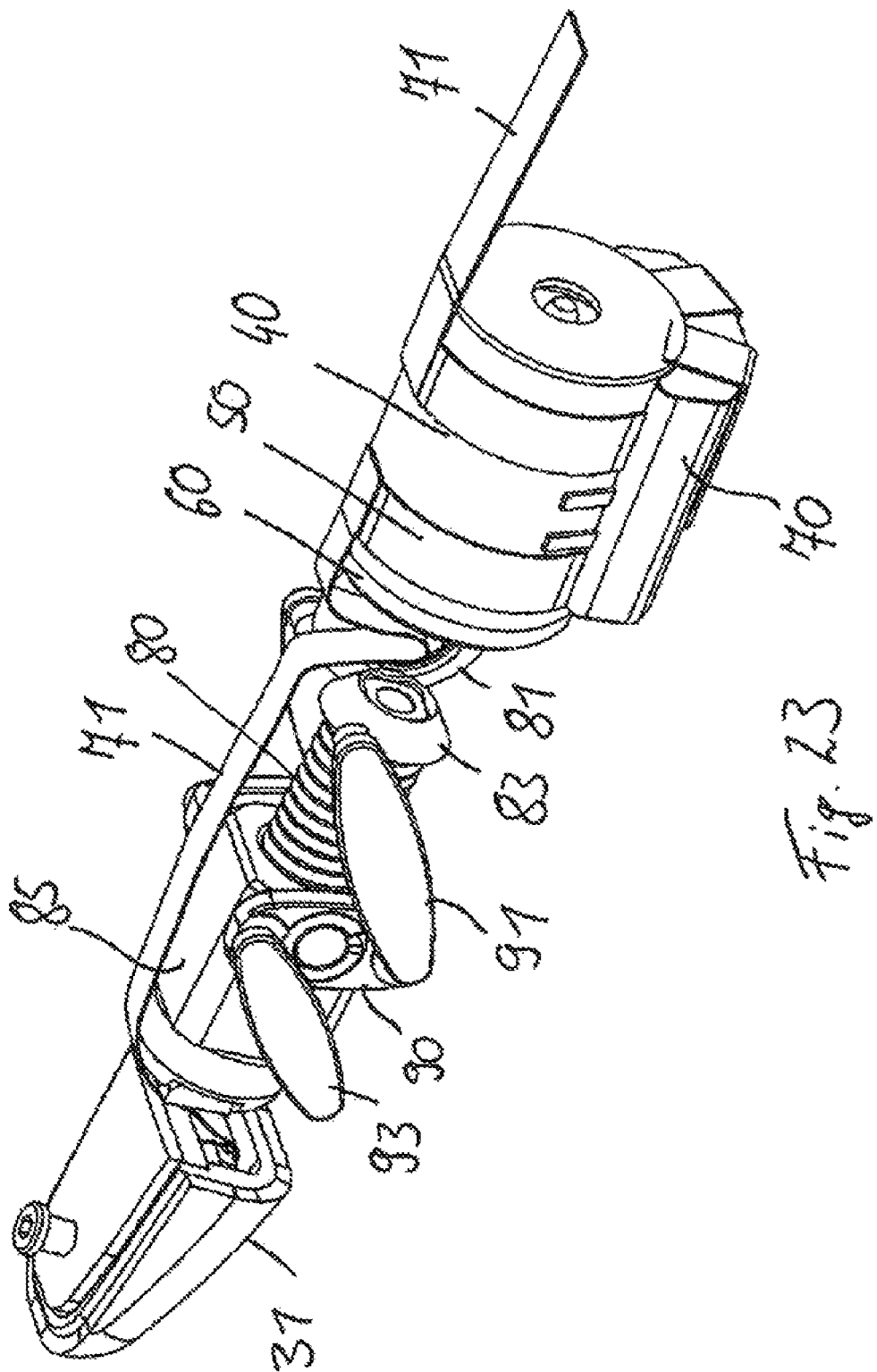

PROSTHETIC FINGER

FIELD OF THE INVENTION

The invention relates to a prosthetic finger with a proximal member, a medial member and a distal member that are mounted pivotably in one another, and with a motor which is arranged in the prosthetic finger and which, via a gear mechanism, rotates the medial member relative to the proximal member. A prosthetic finger of this kind is suitable in particular for artificial hands.

BACKGROUND OF THE INVENTION

In modern prosthetics, the continuing advances that are being made in neuronal coupling of corresponding drive mechanisms are placing increasing demands on separate actuation of individual components. In addition to the usual requirements for a prosthesis that is as light as possible and that is reliable and also inexpensive, it is desirable for the functioning of the prosthesis to approximate as closely as possible to that of the part of the body that is to be replaced. The prosthesis should as far as possible permit all the activities that are permitted by the replaced part of the body. This generally requires a multiplicity of drive mechanisms and control devices and a greater number of joints.

In the case of hand prostheses in particular, the filigree structure of the hand and its extraordinary flexibility place great demands on a corresponding prosthesis.

For example, in order to move prosthetic fingers relative to a chassis, the chassis or a forearm prosthesis is provided with drive mechanisms that move the prosthetic finger in the palmar and dorsal directions via tensioning means. The tensioning means thus assume the role of the human tendons.

To permit more precise control of the prosthetic finger movement, where the fingers are so compact in size and dimension that they correspond as closely as possible to the human fingers, DE 198 54 762 A1 proposes that a motor is arranged in the proximal and medial members of the finger and that the motor pivots the respective next member of the prosthetic finger via a gear mechanism. This is controlled by neuronal signals. A motor that pivots the distal member is arranged in the medial member. An extension part, which can be connected to an artificial finger pad, is coupled to a fixed toothed wheel via a toothed gear with coupling toothed wheels. When the motor of the medial member of the finger is switched on, the distal member of the finger moves up or down. Corresponding to the movement of the coupling toothed wheels, the extension part tilts up or down. The gear arrangement of the distal member of the finger compensates the relatively long lever that is formed by the connecting member and the extension part. If an object is gripped and secured with the finger pad, the distal member of the finger remains fixed in the corresponding position by virtue of its wormwheel coupling, even after the motor of the medial member of the finger has been switched off.

This arrangement requires a large number of parts, in particular a large number of motors and gear wheels, such that the construction as a whole is complex.

SUMMARY

The object of the present invention is to make available a prosthetic finger that is made lighter in weight without adversely affecting its functionality.

According to the invention, this object is achieved by a prosthetic finger having the features of claim 1. Advantageous embodiments and developments are set forth in the dependent claims.

The prosthetic finger according to the invention, with a proximal member, a medial member and a distal member that are mounted pivotably in one another, and with a motor which is arranged in the prosthetic finger and which, via a gear unit, rotates the medial member relative to the proximal member, is characterized in that the medial member accommodates a longitudinally movable balance arm which is connected via levers to the proximal member and to the distal member. The longitudinally displaceable design of the balance arm, which is connected by adjustment levers both to the proximal member and also to the distal member, ensures that two members of a finger can be moved uniformly by only one drive, such that the finger unwinds harmonically. Two joints are moved by just one drive unit, such that a complete mobility of the prosthetic finger is afforded despite the presence of a subactuated system with two degrees of freedom and one degree of movement. For reasons of weight distribution, the motor is preferably mounted in the proximal member, although it can also be accommodated in the medial member. An arrangement in the distal member is also possible in principle, but this would move the center of gravity very far away from the bearing of the prosthetic finger and, because of the confined space, would only permit accommodation of a small motor and, therefore, a low gripping force.

The balance arm is preferably mounted or arranged on a spindle nut which moves along the longitudinal extent of the medial member during rotation of the driven spindle. The direction of movement is dependent on the direction of rotation of the spindle. The rotation movement of the spindle about an axis parallel to the longitudinal extent of the medial member has the effect that the spindle nut, together with the balance arm mounted thereon, can be easily moved in translation. The set-up of the balance arm kinematics permits a compact structure, as a result of which the individual components in their geometric dimensions can be accommodated within the contour of a normal medial member.

The motor is coupled to the spindle, which is mounted movably in rotation in the medial member. The spindle is preferably mounted on a central axis of the medial member such that a symmetrical set-up of the prosthetic finger can be achieved. All eccentric arrangement of the spindle may also be provided.

To reduce the friction losses, the spindle is designed as a recirculating ball spindle, such that a very high degree of efficiency can be achieved by virtue of the low friction between the spindle and the spindle nut. In this way, only a motor of correspondingly small dimensions is needed for the drive, with the result that the drive and the spindle with the spindle nut can be made very light in weight. Because of the lack of self-locking of the recirculating ball spindle, further measures have to be taken to ensure that the motor is not damaged by loading on the output side.

To ensure a symmetrical distribution of forces within the prosthetic finger, the levers that connect the spindle nut to the proximal member and to the distal member are preferably arranged on both sides of the spindle nut, such that the spindle nut cannot tilt and become jammed.

The spindle and the motor are preferably coupled to each other via a bevel gear, in which case, when the motor is arranged in the proximal member, a coupling bevel wheel is mounted on the proximal member about the rotation axis of the medial joint. In this way, via a bevel wheel arranged on the output shaft of the motor, it is possible to drive the spindle, which also has a bevel wheel, in a manner independent of the angle of rotation.

Analogously to the solution with levers arranged on both sides, provision is made for two balance arms to be arranged on both sides of the spindle nut, in order to obtain a uniform distribution of forces. In order to synchronize the movement of the distal and proximal levers, the balance arms are coupled to each other, such that the two balance arms form a bridge or a frame around the spindle nut.

The balance arms can either be fixed at a fixed angle to the direction of movement, secured in a rotationally fixed manner on the spindle nut in the case of an arrangement on a spindle nut, or can be designed to pivot about a fixed angle to the direction of movement, so as to be able to compensate for non-uniformity of the flexion movement of the medial and distal joints. When the balance arm is mounted movably, for example on the spindle nut, provision is advantageously made that a normal position is maintained by spring pretensioning. For this purpose, the balance arm is supported elastically in relation to the spindle nut. In principle, it is also possible that pivoting is permitted in both directions of rotation, starting from the normal position, and that elastic elements, for example springs or plastic or rubber parts, keep the balance arm pretensioned in the normal position. If the finger is now moved with idling load, that is to say before the medial and distal joints are placed about an object, the balance arm is maintained at the angle. When the medial or distal member touches an object and the respective other member of the prosthetic finger is not stopped by an object, the respective unstopped member of the prosthetic finger continues to move, since the spindle nut is moved further. By permitting a change in the angular position of the balance arm relative to the direction of movement, the respective member of the prosthetic finger not yet in contact can continue to move to a limited extent. In this way, a non-uniform bending of the medial member and distal member can take place, such that the coupling via the balance arm lever system functions as a differential. The spring pretensioning can be generated by a spring element that has a linear or preferably progressive characteristic curve, such that a corresponding ratio is achieved between the rotation angle of the balance arm and the restoring moment.

In a development of the invention, the spindle is mounted so as to be axially movable and is provided, preferably at the distal end, with a blocking mechanism which engages with and locks the spindle when a fixed displacement path is exceeded. The blocking mechanism can be designed as a form-fit brake or friction brake, which prevents a further rotation movement of the recirculating ball spindle when an output-side moment is introduced via the distal member. In one embodiment of this blocking mechanism, the latter is designed as an elastic recess with friction surfaces of form-fit elements. The spindle can be mounted in the blocking mechanism such that the blocking mechanism serves at the same time as a bearing location. When an output-side moment is introduced, the spindle moves distally and then comes into engagement with the friction-fit or form-fit elements and prevents further movement. Inside the blocking mechanism, the spindle can be provided with a ball bearing, such that drive can take place with the least possible friction during normal operation.

To be able to mount the spindle such that it can be displaced longitudinally when corresponding load situations arise, it is mounted on the bevel wheel in a longitudinally displaceable and rotationally fixed manner, such that the spindle-side bevel wheel mounted on the coupling bevel wheel always remains in engagement. The longitudinally displaceable and rotationally fixed bearing can be effected by a polygonal toothing.

In a development of the invention, sensor devices are arranged on each joint in order to detect the angular positions of the respective member of the prosthetic finger. Likewise, sensor devices can be provided for detecting the loading of the respective structural parts, in particular the torques or bending moments by means of strain gauges. In the distal member, a sensor is arranged with a distal and/or palmar orientation, in order to detect contact of the prosthetic finger with an object and, if appropriate, to be able to send a message back to the prosthesis user.

A control electronics unit of the motor and evaluation unit are likewise arranged in the prosthetic finger, so as to permit control and evaluation of the sensor data autonomously of the prosthetic finger. The prosthetic finger can therefore be constructed and manufactured as a structural unit, which then only has to be connected mechanically to a chassis and to a bus connection, for forwarding the control data and sensor data, and to a power supply. The proximal member can likewise be mounted and driven on the chassis. The control electronics unit is preferably arranged in the prosthetic finger, e.g. in the proximal member, in particular below the motor. In order to connect the control unit to the sensors, a flexible conductor track is provided that connects the electronics unit to sensors.

The motor can be coupled to a step-down gear, which is preferably designed as a friction gear. In this case, motor and gear are designed as a structural unit so as to achieve the smallest possible overall size. The output of the motor is via a motor shaft, which is mounted at the proximal end on a motor housing and at the distal end inside the friction gear. In this way, a second bearing site inside the motor is dispensed with, which reduces the overall length of the motor/gear unit.

The motor, if appropriate the motor/gear unit, is followed by a detent which blocks the introduction of a load on the output side and conveys only drive-side moments. In this way, the adopted position of the finger can be maintained if the power supply fails or if the motor is switched off. Self-locking of the drive, and an associated increase in power loss, is therefore no longer needed. The detent is preferably designed as clamping roller freewheels, which act in both directions of rotation, and it is preferably released by actuation of the motor. The detent can likewise be integrated in the motor/gear unit, in which case the detent is mounted via balls on a roller holder of the clamping roller freewheel of the detent. The motor, the gear and the detent are designed as a structural unit and can also be used to drive other mechanisms. A friction gear has the advantage of operating quietly.

DESCRIPTION OF THE DRAWINGS

Identical reference signs in the figures designate identical components.

FIG. 21 shows a sectional view of the distal end of the spindle bearing;

FIG. 22 shows a perspective oblique view of a medial member from above; and

FIG. 23 shows a view of the mechanical components of the prosthetic finger without frame parts.

DESCRIPTION

Figure 1:
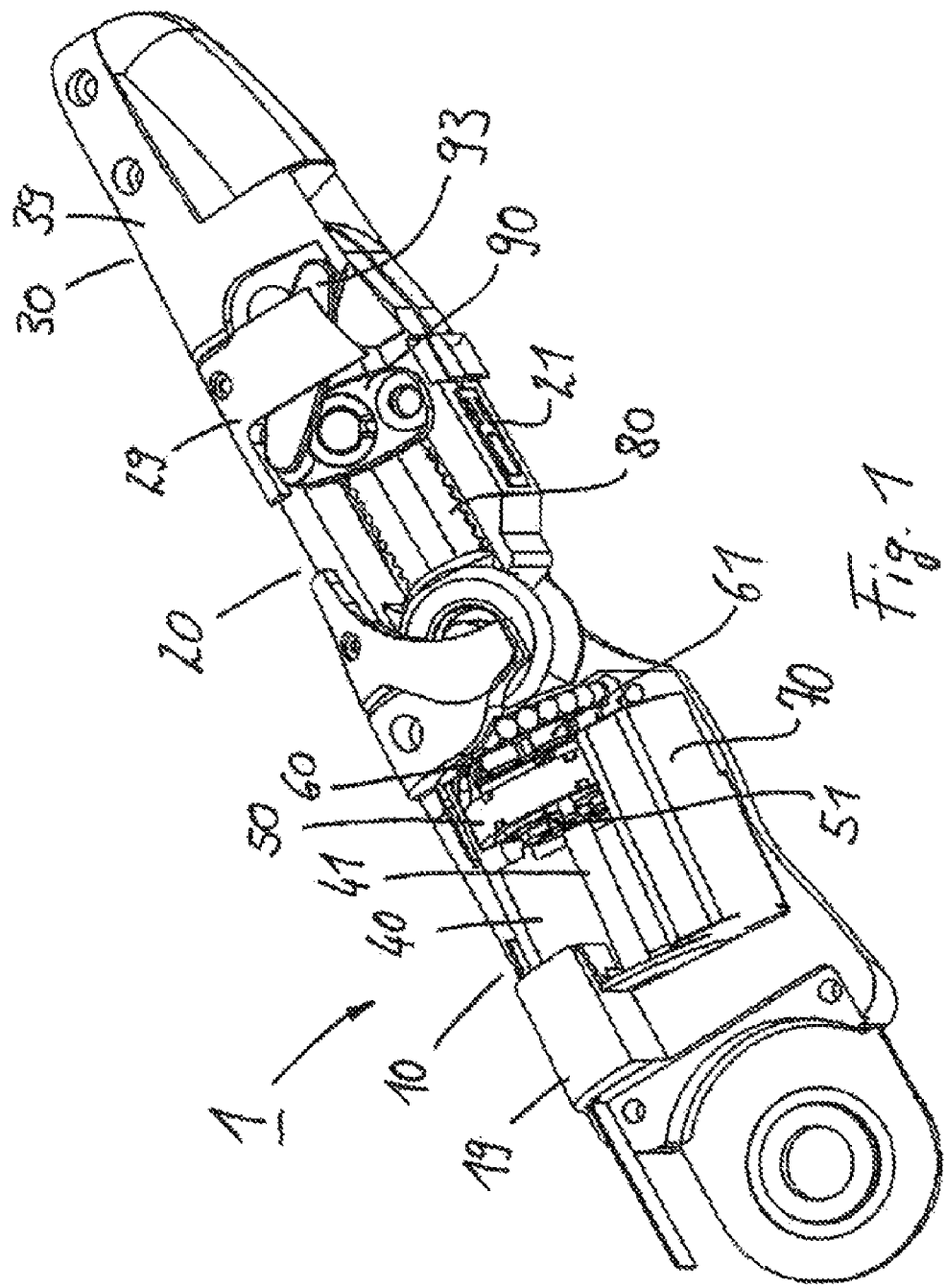
FIG. 1 shows a partial sectional view of prosthetic finger.

In FIG. 1, a prosthetic finger 1 with a proximal member 10, a medial member 20 and a distal member 30 is shown in a partial sectional view. The proximal member 10 can be secured on a chassis (not shown) so as to be driven in an articulated manner. The connection and the drive mechanism of the proximal member 10 is not shown.

Figure 2:
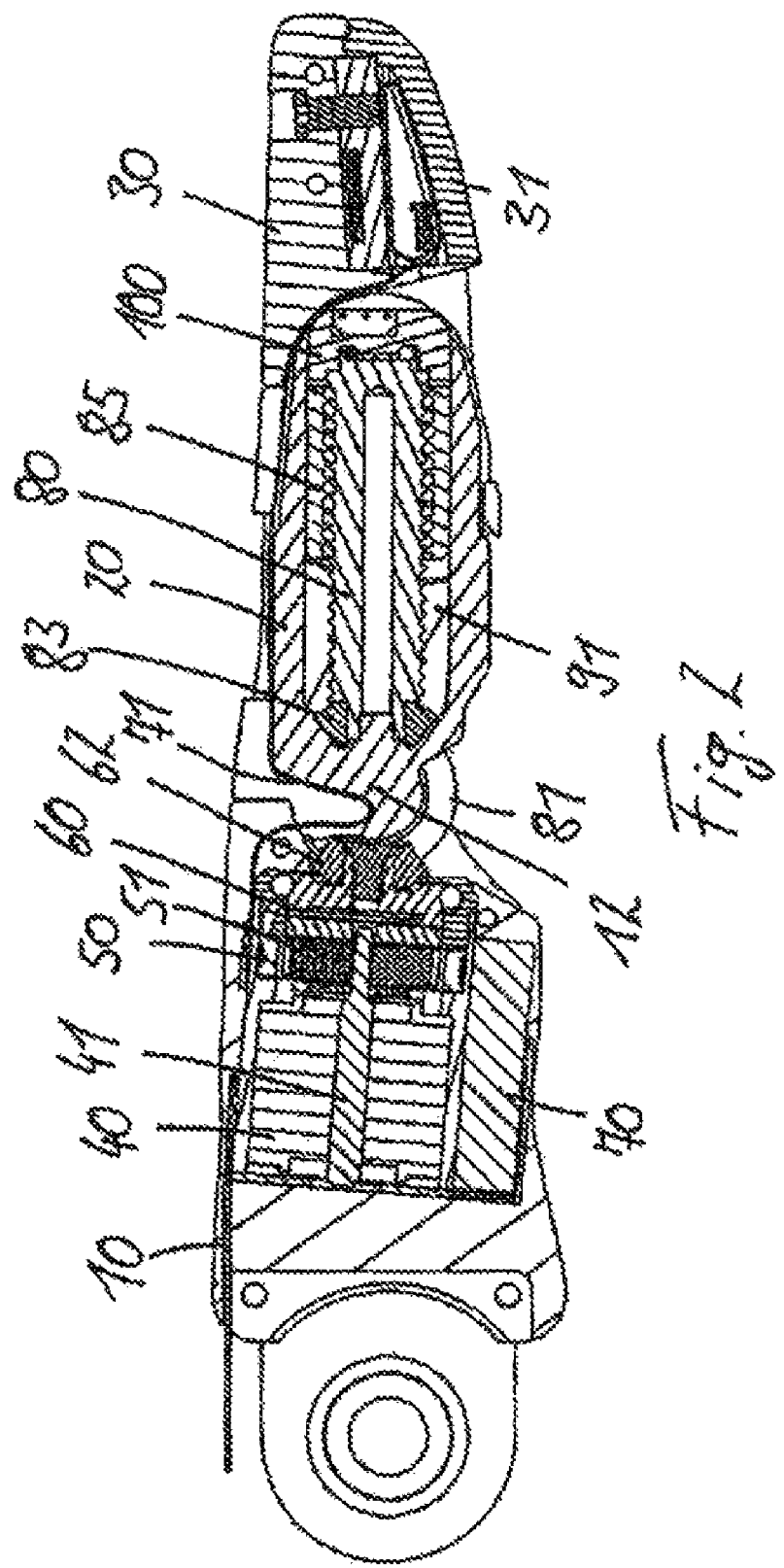
FIG. 2 shows a sectional view of a prosthetic finger in a longitudinal plane.

The proximal member 10 accommodates a motor 40 with an output shaft 41 that engages in a friction gear 50 with friction wheels 51. A detent 60 with clamping rollers 61 is driven via the friction gear 50 and is in turn coupled to an output bevel wheel. The output bevel wheel is shown in FIG. 2 and is designated by reference sign 62. The output bevel wheel 62 engages in a coupling bevel wheel 81, which is mounted pivotably about a rotation axis 12 of the medial member 20 about the proximal member 10. The coupling bevel wheel 81 drives an output bevel wheel 83 mounted on a spindle 80 in a rotationally fixed manner. The spindle 80 is mounted on the medial member 20 and is designed in the present case as a recirculating ball spindle. A spindle nut 85 is mounted on the recirculating ball spindle 80 and, depending on the direction of rotation of the spindle 80, is moved in the direction of the distal end or proximal end of the spindle 80. The spindle nut 85 is therefore mounted in a longitudinally displaceable and rotationally fixed manner inside the medial member 20. A blocking mechanism 100, which is explained in more detail below, is secured on the distal end of the spindle 80.

A distal member 30 is arranged in an articulated manner on the distal end of the medial member 20.

A balance arm 90 is arranged on the spindle nut 85 and is arranged at a substantially fixed angle with respect to the longitudinal direction of the spindle 80. Formed on the palmar and dorsal end of the balance arm 90, recesses for levers 91, 93 permit transmission of tension and pressure and rotation of the levers 91, 93 within the recesses. The levers 91, 93 are arranged on the proximal member 10 and the distal member 30, respectively. In the present embodiment, the lever 91, which connects the proximal member 10 to the balance arm 90, is arranged on the dorsal face of the proximal member 10 and on the palmar face of the balance arm 90, whereas the lever 93, which connects the distal member 30 to the balance arm 90, is secured on the dorsal face of the balance arm 90 and on the palmar face of the distal member 30, the terms dorsal and palmar relating to the arrangement relative to the rotation axes of the members of the prosthetic finger.

In FIG. 1, the prosthetic finger 1 is shown in the extended position. The movable parts are covered sectionally by covers 19, 29, 39 and protected by them, and the housings 19, 29, 39 and the individual members 10, 20, 30 are designed such that a corresponding pivoting of the members 10, 20, 30 to one another is permitted.

Underneath the motor 40, there is a control device 70 or electronics unit which is connected to sensor devices (which will be explained below) via a flexible conductor 71, which is shaped as a loop at the joint areas.

Figure 3:
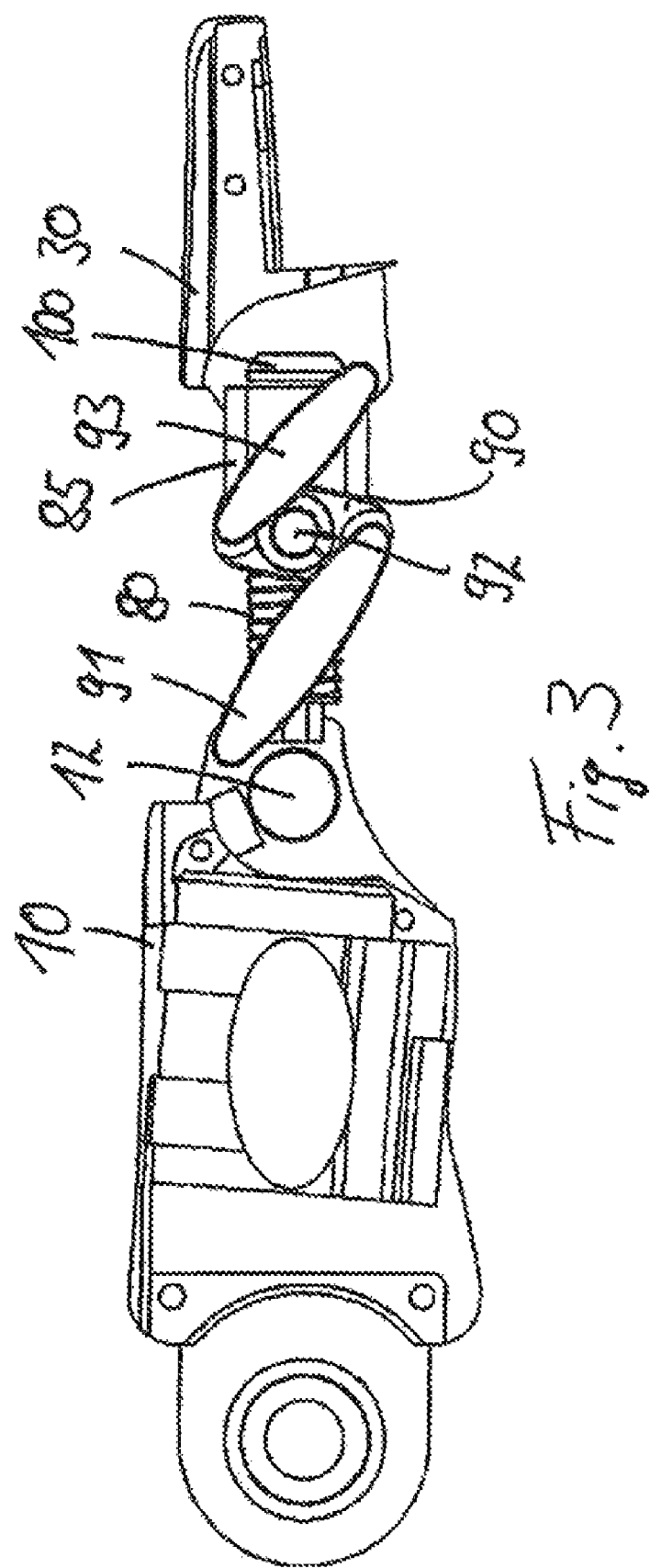
FIG. 3 shows a detailed view of a balance arm gear in the extended position.

The adjustment mechanism inside the medial member 20 is shown on its own in FIG. 3. The drive mechanisms and the gear elements have been cut away for the sake of clarity. The spindle 80, which can be designed as a normal spindle instead of as a recirculating ball spindle, is mounted rotatably inside the medial member 20. The bearing at the distal end can be formed by a blocking mechanism 100, e.g. in the shape of an elastic cap, whose function will be explained below. The levers 91, 92, stable to tension and pressure, are secured on the dorsal face and palmar face at the dorsal end of the balance arm 90, which is arranged on a pin 92 of the spindle nut 85. The connecting lever 91 to the proximal member 10 is secured dorsally of the rotation axis 12 on the proximal member 10, whereas it is arranged on the balance arm 90 on the palmar face, that is to say below the rotation axis 12. The connecting lever 93 is mounted on the distal member 30 in the same orientation, wherein the securing site on the balance arm 90 is articulated above the rotation axis of the distal member 30, while that on the distal member 30 itself is articulated below the rotation axis. If the recirculating ball spindle 80 is now driven clockwise, as seen in the distal direction, the spindle nut 85, which is mounted through the levers 91, 93 or through a recess of the inner wall of the medial member 20 and in which the recirculating balls turn, is moved in the proximal direction. It is shown in the middle position in FIG. 4.

Figure 4:
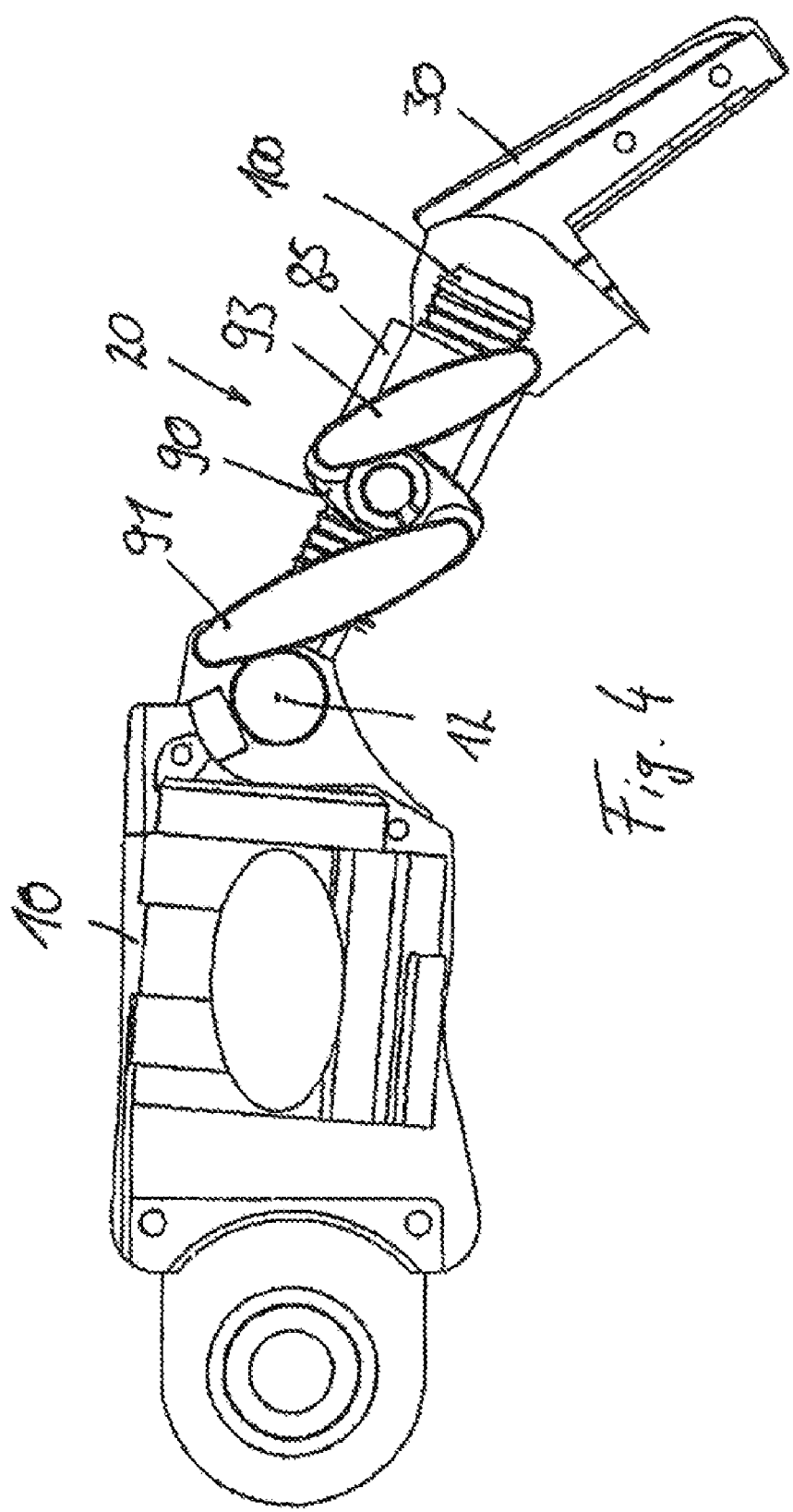
FIG. 4 shows a view of FIG. 3 in a slightly flexed position.

FIG. 4 shows the prosthetic finger 1 in a slightly angled position in which the medial member 20, whose lengthwise extension corresponds with the lengthwise extension of the recirculating ball spindle 80, is pivoted dorsally by approximately 45° relative to the extended position. This results from the geometry of the articulation points of the levers 91, 93 on the balance arm 90 and on the distal member 30 or proximal member 10. Because of the substantially rotationally rigid orientation of the balance arm 90 on the spindle nut 85, the distal member 30 is pivoted relative to the medial member 20 at the same time as the medial member 20 is pivoted relative to the proximal member 10. There is therefore a movement coupling of the lever system of the balance arm lever kinematics, such that a harmonic flexion movement is executed upon flexion of the medial member 20 together with the distal member 30.

Figure 5:
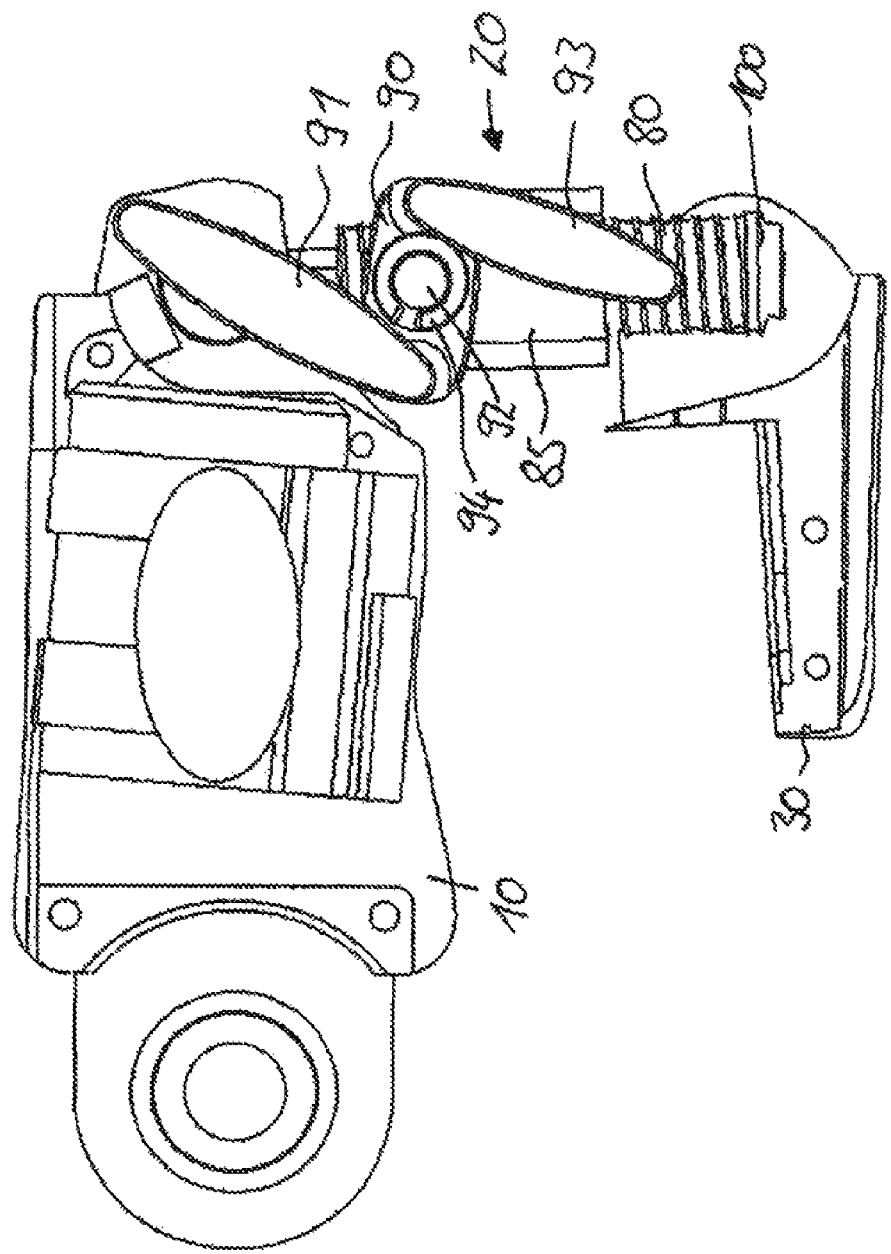
FIG. 5 shows a view of the prosthetic finger in the position of maximum flexion.

The prosthetic finger 1 is shown in FIG. 5 with the finger at an angle. The distal member 30 is almost parallel to the proximal member 10, and the spindle nut 85 has moved almost completely in the direction of the proximal member 10, such that the medial member 20 and also the distal member 30 are each almost at right angles to the proximally arranged member.

By means of the chosen arrangement of the levers 91, 93 on the proximal member 10 and distal member 30 and of the respective articulation points of the levers 91, 93 on the proximal member 10 and distal member 30, and of the dimensioning of the balance arm 90, it is possible to ensure that the levers 91, 93 do not pass through the rotation axes 12, 23 of the medial member 20 or distal member 30, such that a dead-center position is avoided. If such a dead-center position is wanted, the levers 91, 93 would have to pass through the rotation axes 12, 23.

If the balance arm 90 is arranged in a rotationally fixed manner on the spindle nut 85, there is then a fixed ratio between the pivoting movements of the medial member 20 and of the distal member 30. By arranging the levers 91, 93 in another way, it is possible to permit a faster advance of the medial member 20, so as to permit an end position of the prosthetic finger 1 that approximates more to the natural position. Such a position would be reached when the medial member 20 in an end position is oriented at 120° to the proximal member 10 and the distal member 30 in an end position is oriented at 90° to the medial member 20.

It will be seen from FIGS. 3 to 5 that a spring 94 holds the balance arm 90 in a normal position with respect to an abutment, which will be explained below. This permits easy rotation of the balance arm 90, in this case in a counterclockwise direction, such that, when the medial member 20 makes contact with an object and the medial member 20 is thus unable to continue its movement, the angular position of the balance arm 90 relative to the longitudinal axis of movement changes. In this way, the position of the point of articulation of the lever 93 is changed by the rotation of the balance arm 90, such that the distal member 30 can continue to move over a limited range, which is defined by the size of the angle of movement of the balance arm 90. In addition to the design by means of a spring 94 and only one free direction of rotation of the balance arm, it is in principle also possible to have an elastic bearing on both sides, for example by an elastomer element or by springs, so as to permit resiliency and tracking in both directions.

Figure 6:
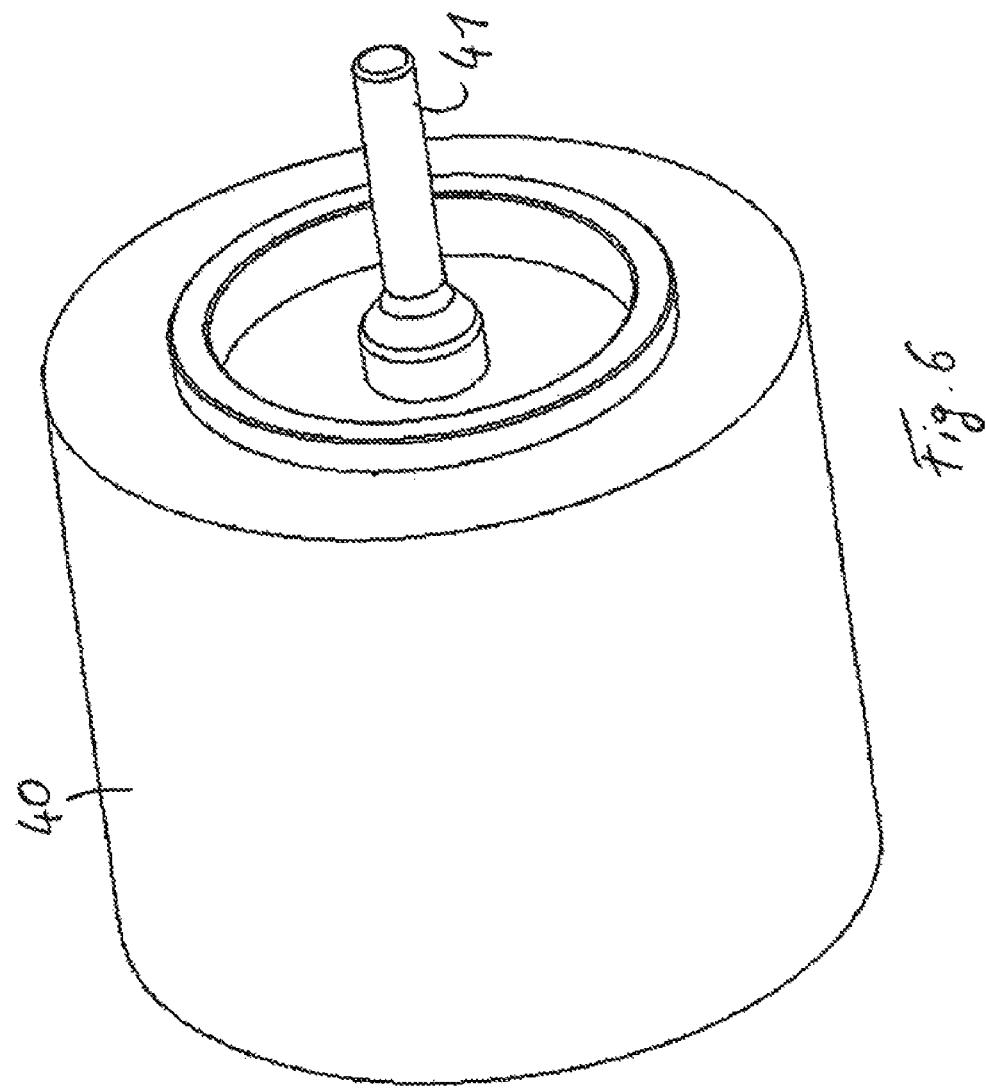
FIG. 6 shows a view of the motor unit.
Figure 7:
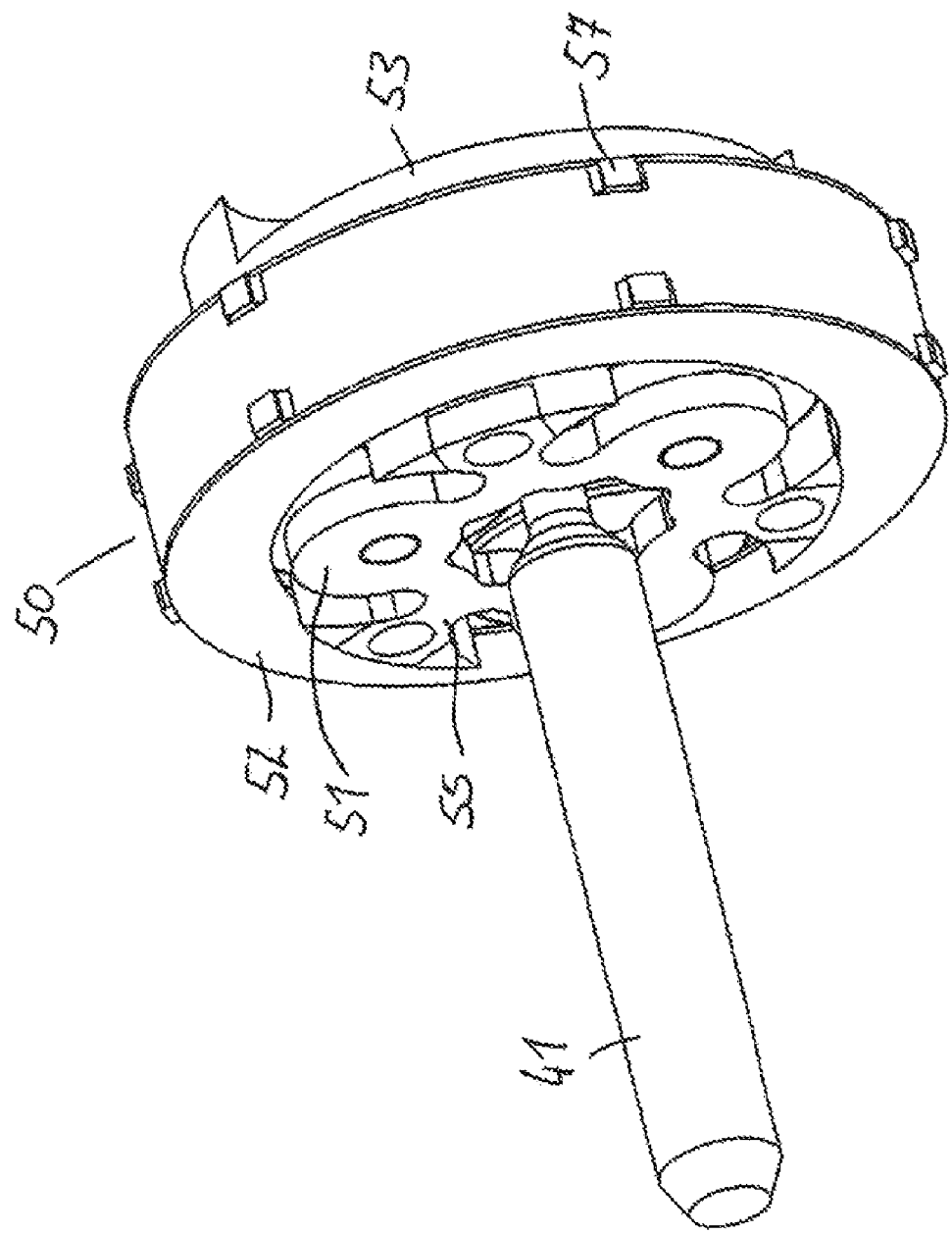
FIG. 7 shows a detailed view of a friction gear.

FIG. 6 shows a drive of an electric motor 40 with an output shaft 41. FIG. 7 shows the output shaft 41, in the assembled state, projects into a friction gear 50, which in the present case has three friction wheels 51 that run inside a raceway 52. The output 53 is shown on the side directed away from the motor 40 (not shown). On the outer circumference of the friction gear 50 there are projections 57 with which the raceway 52 can be mounted in a rotationally fixed manner inside the proximal member.

Figure 8:
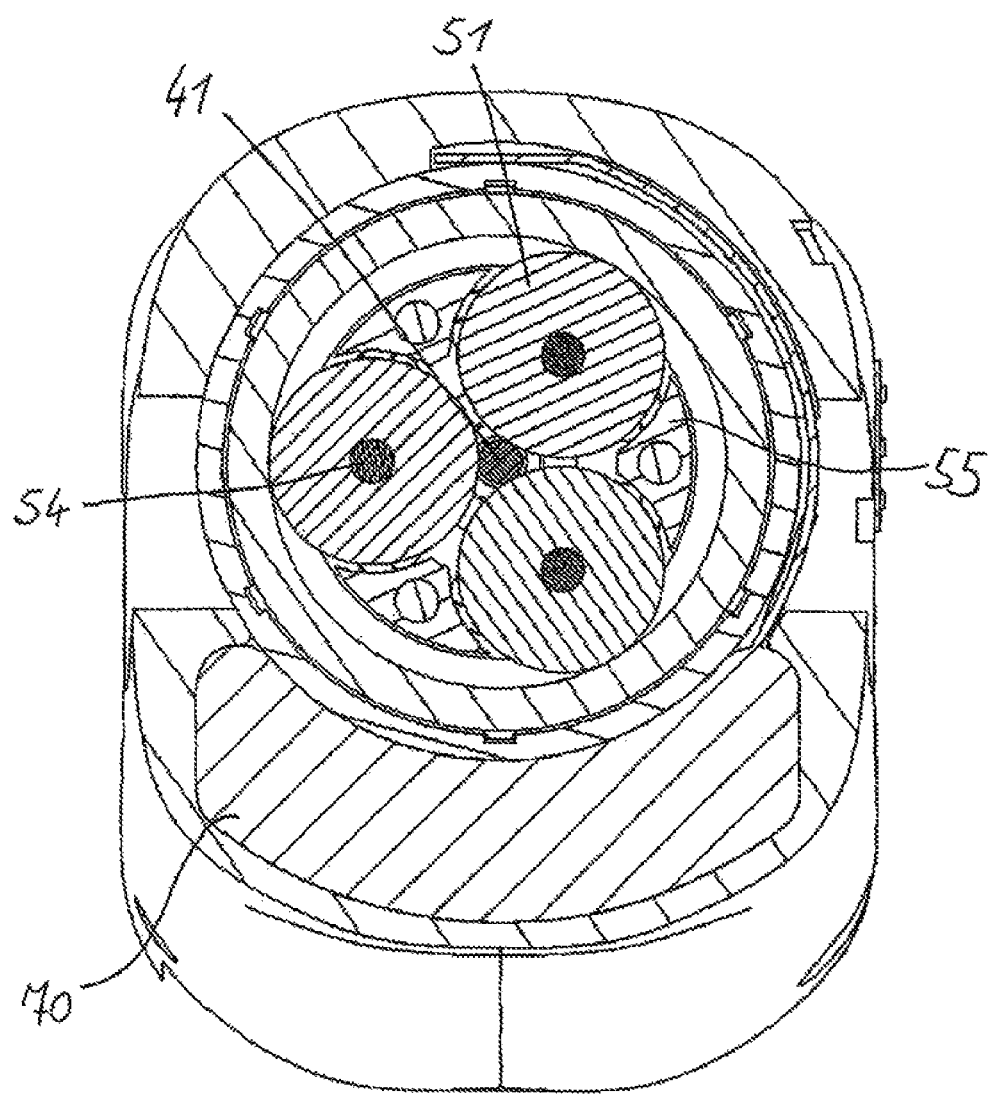
FIG. 8 shows a sectional view of the friction gear according to FIG. 7.

FIG. 8 shows a section perpendicular to the output shaft 41 through the friction gear 50 from the distal direction. The three friction wheels 51 bear on the output shaft 41, thus allowing the friction wheels 51, mounted on shafts 54, to run inside the raceway 52. The control electronics 70 arranged below the motor 40 can be seen clearly in this view.

Figure 9:
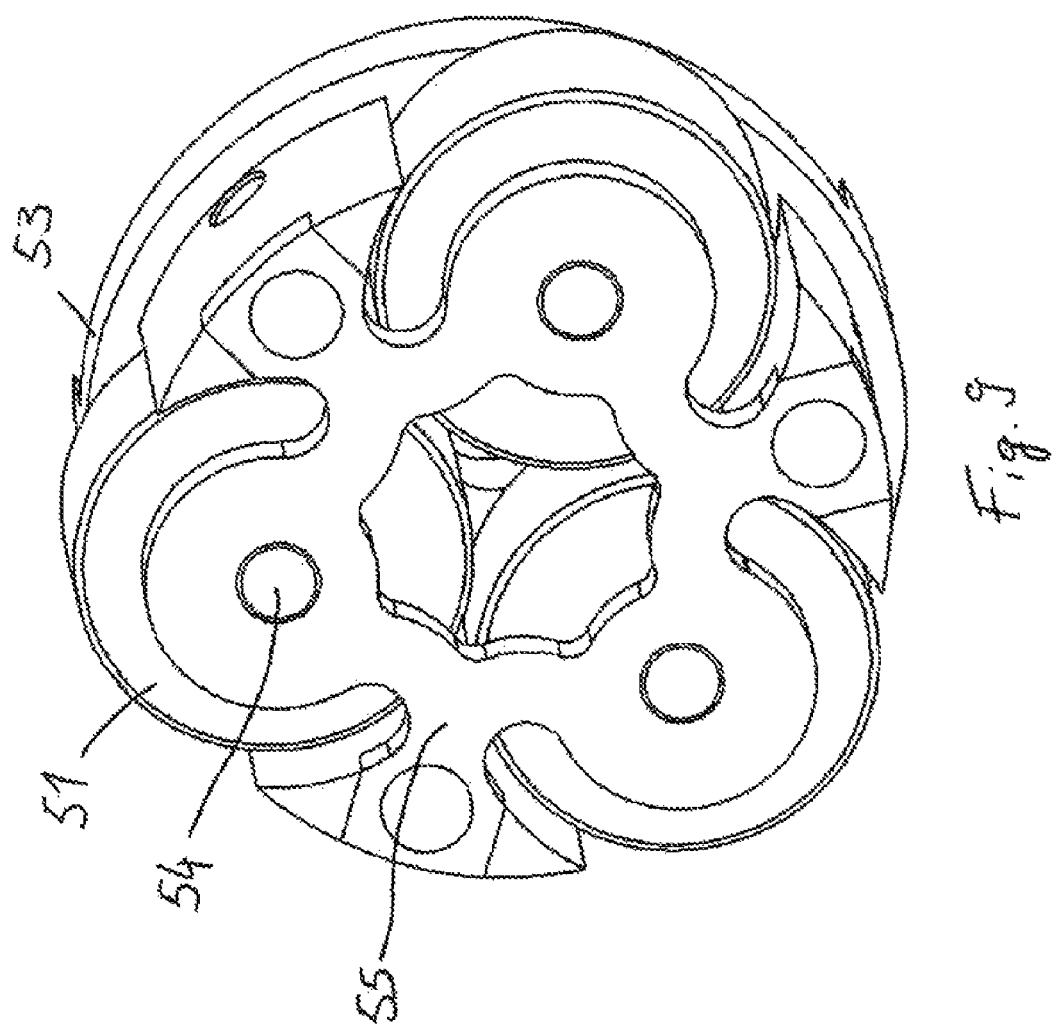
FIG. 9 shows a detailed view of the friction gear.

FIG. 9 shows the drive side of the friction gear 50, with the friction wheels 51 which are mounted on the shafts 54 of a friction wheel support 55, and the output side 53.

Figure 10:
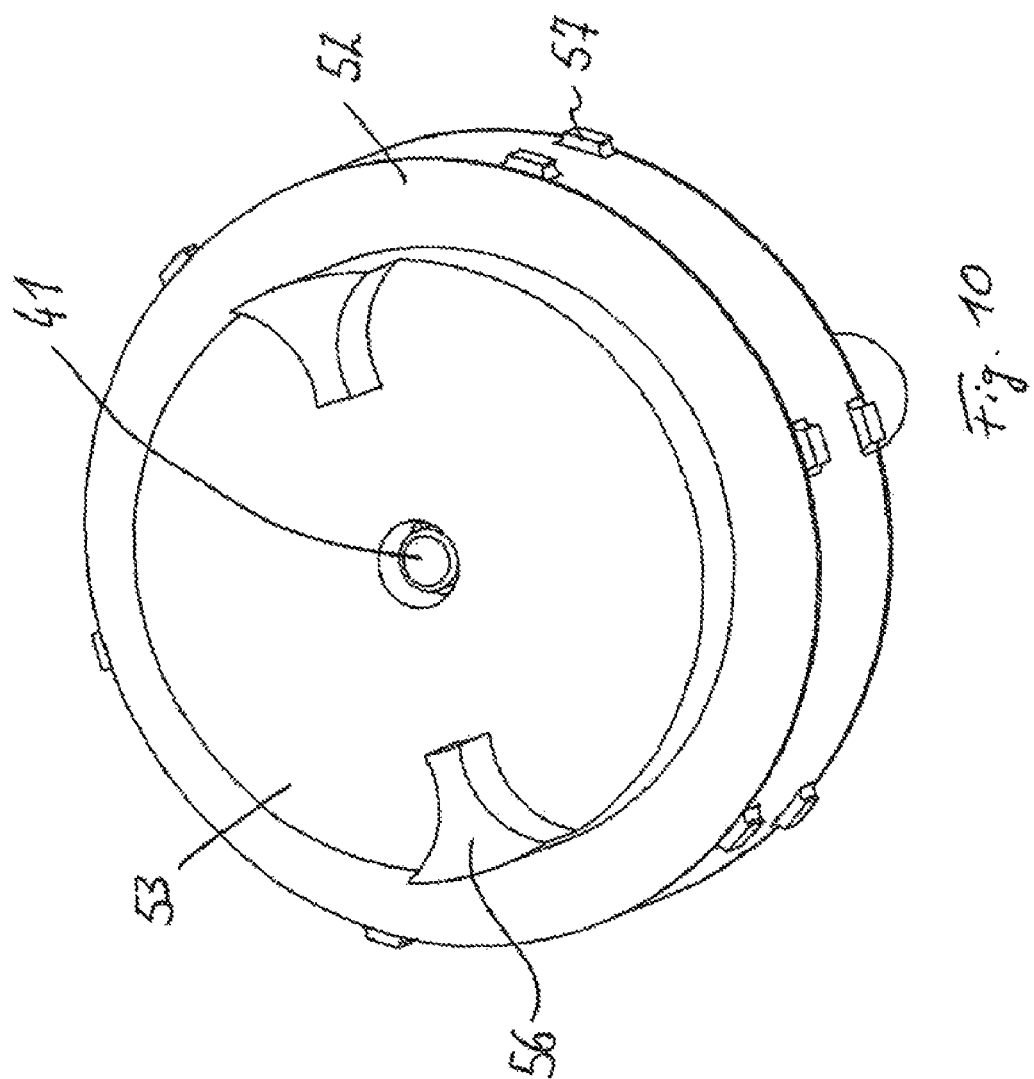
FIG. 10 shows an output-side view of the friction gear.

FIG. 10 shows the output side of the friction gear 50, where the output 53 has axially protruding release elements 56 which at the same time serve to drive a detent 60, which has already been shown in FIGS. 1 and 2.

Figure 11:
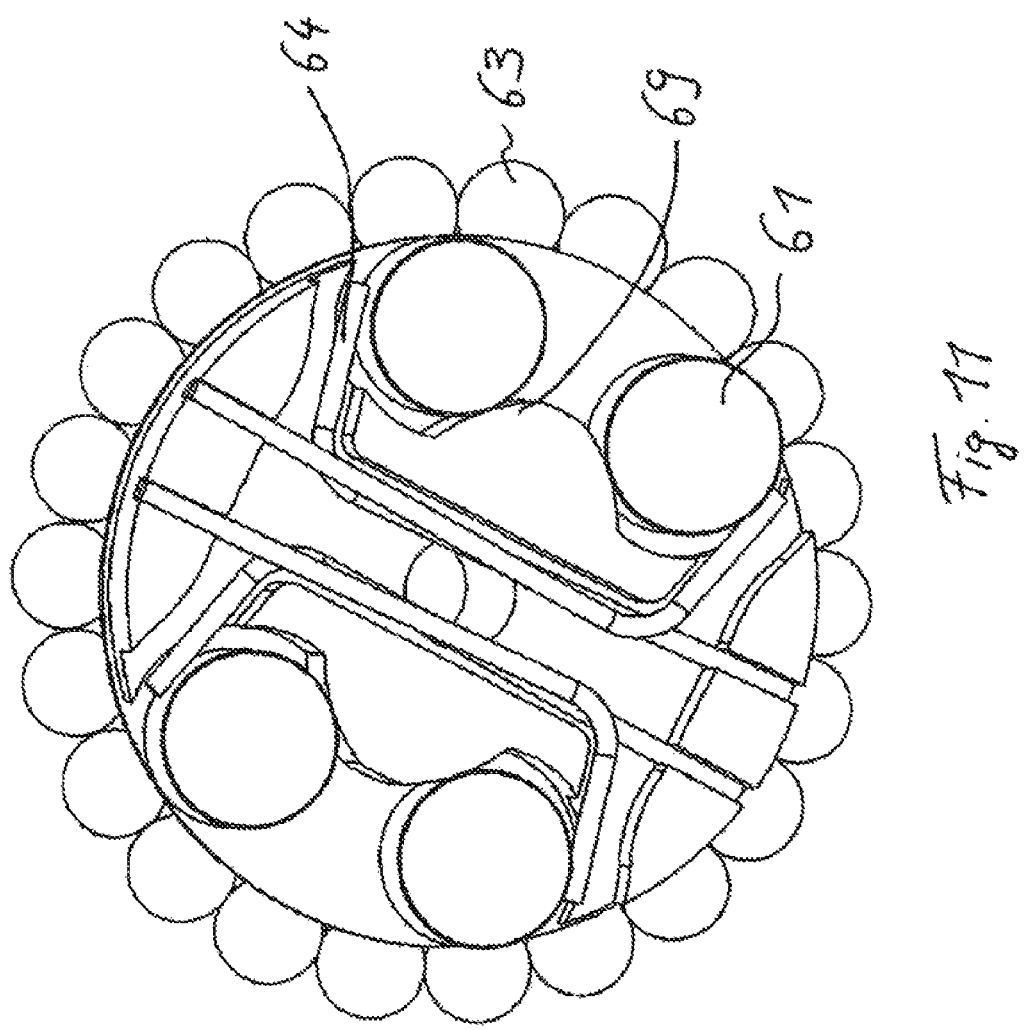
FIG. 11 shows a detailed view of a detent.
Figure 12:
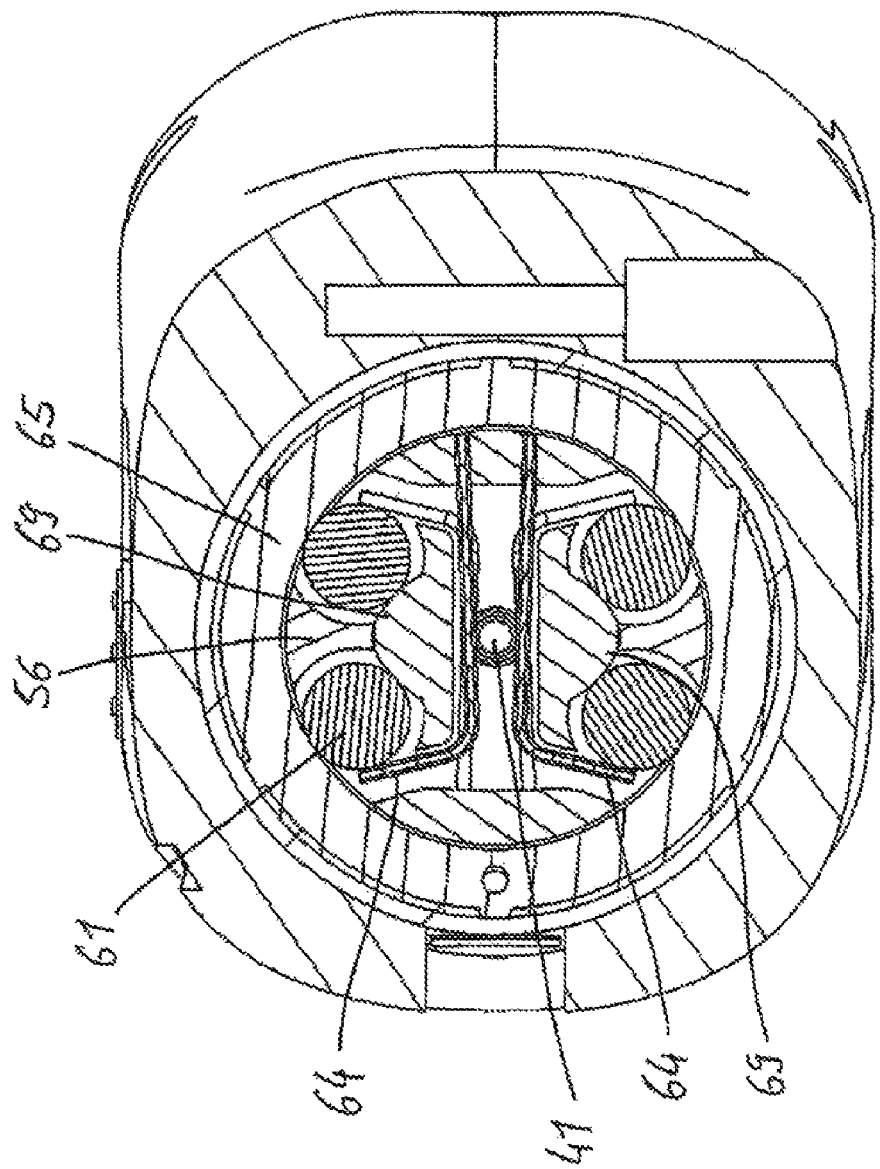
FIG. 12 shows a drive-side plan view of the detent.

FIG. 11 shows the detent 60 with four clamping rollers 61 which, as is shown in FIG. 12, are supported opposite a clamping ring 65. The clamping rollers 61 are pressed against contact shoulders 69 on a support 68 via springs 64, such that, in the absence of a drive moment, they are always in friction contact with the clamping ring 65. If the output element 53 is now turned with the release elements 56 in the clockwise direction, the mutually opposite clamping rollers 61 are pressed against the springs 64 and disengaged from the clamping ring 65, such that the detent 60 can be turned. The clamping rollers 61 not coming into contact with the release element 56 are pressed against the corresponding ends of the springs 64 and run because of the geometric dimensions of the shoulders 69. If the motor 40, and with it also the output 53 of the friction gear 50, is turned in the other direction, the release elements 56 will disengage the obliquely opposite clamping rollers 61.

Figure 13:
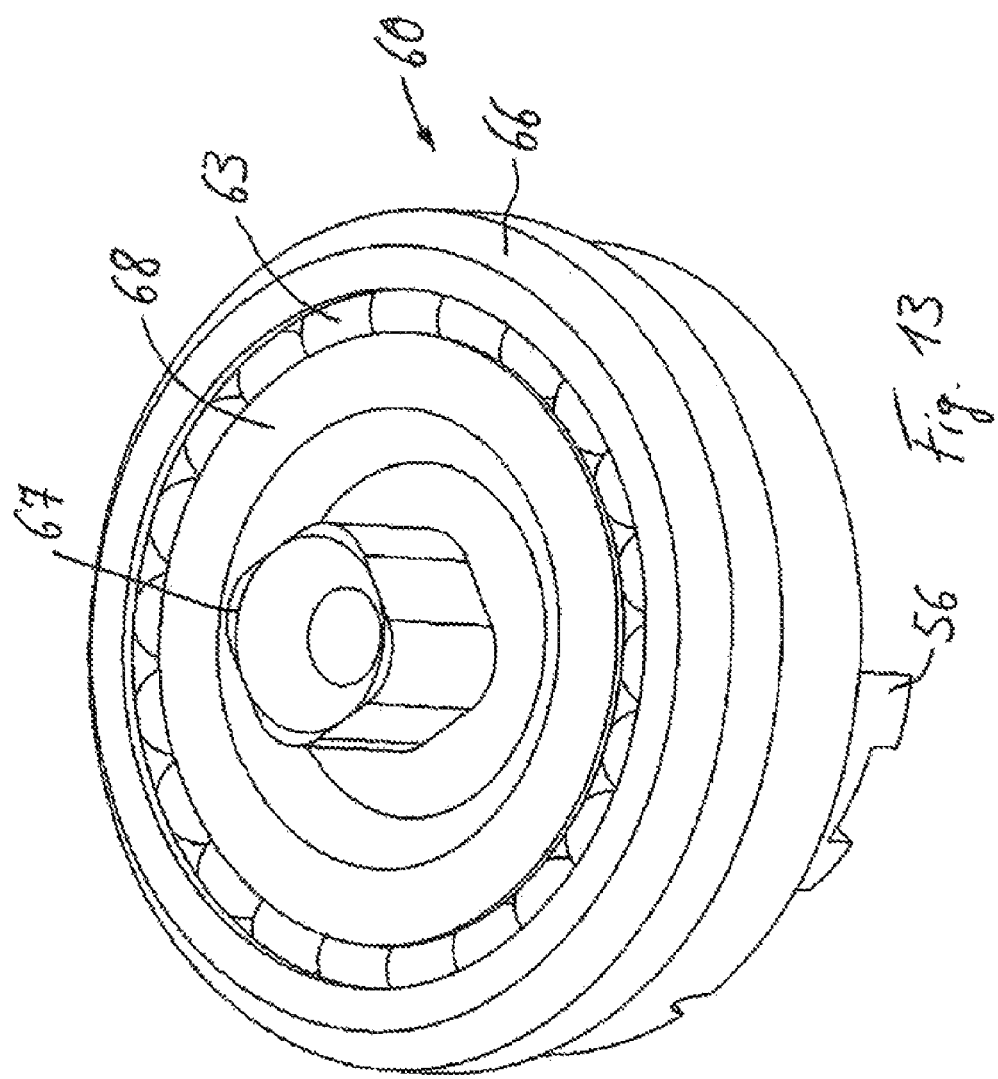
FIG. 13 shows a perspective view of the detent from the output side.

FIG. 13 shows a perspective overall view of the detent 60, which is mounted via balls 63 on the outer bearing ring 66. On the output side of the support 68, there is an output pin 67 onto which an output toothed wheel 62 can be fitted.

Figure 14:
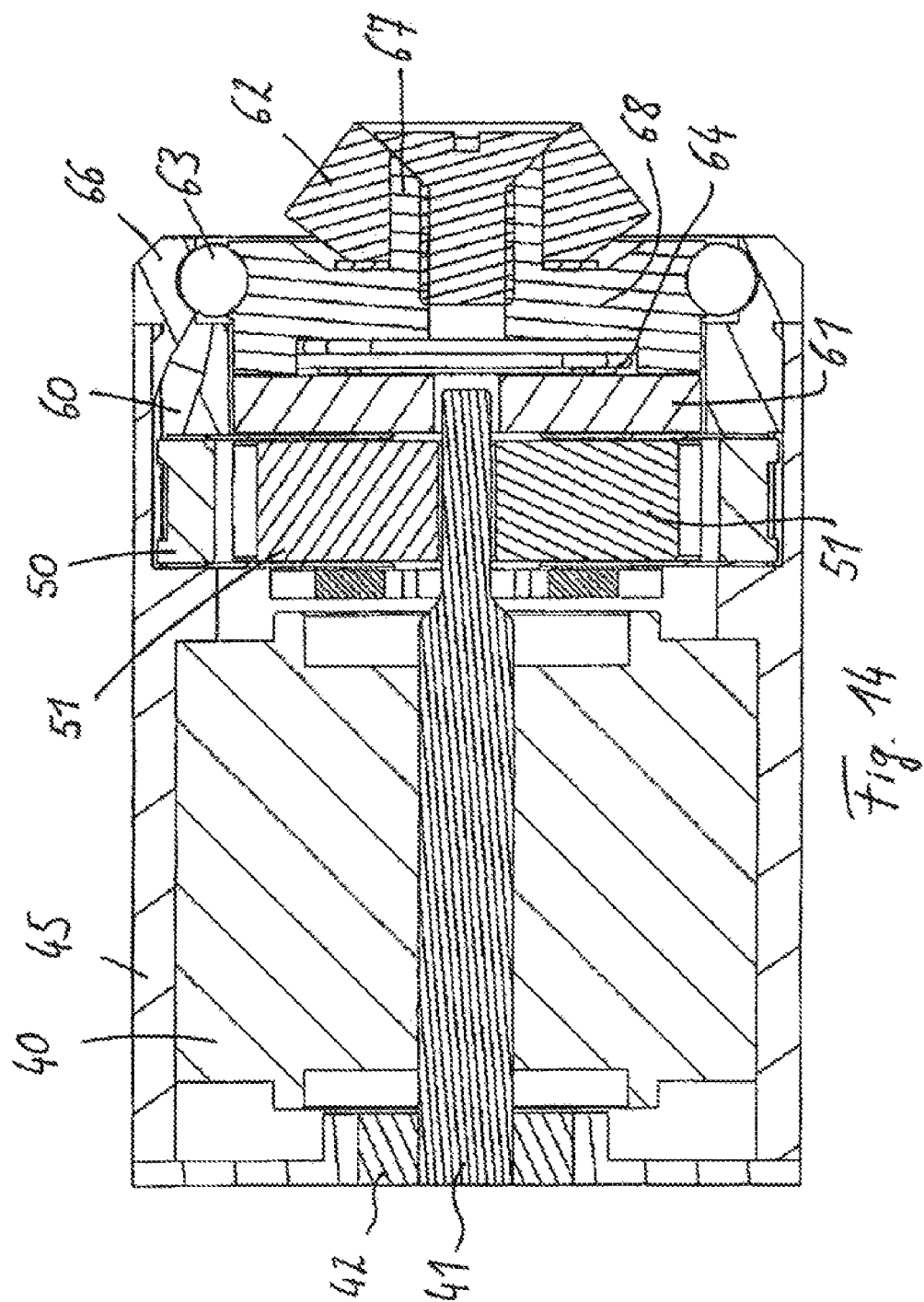
FIG. 14 shows a sectional view through the motor/gear/detent unit.

FIG. 14 shows a sectional view into the structural unit composed of motor 40, friction gear 50 and detent 60, which are accommodated in a common housing 45. An output bevel wheel 62 is mounted and secured on the output pin 67. If a moment is now introduced on the output side via the output toothed wheel 62, the clamping rollers 61 wedge with the clamping ring 65, such that the friction gear 50 and the motor cannot move. This fixing is necessary because the spindle 80, which is designed as a recirculating ball spindle, has a very high degree of action without self-locking tendency. The outer bearing of the detent 60 via the balls 63 in the bearing ring 66 serves for additional fixing and orientation of the output bevel wheel 62. It can also be seen in FIG. 14 that the output shaft 41 of the motor 40 is mounted proximally on the housing 45 of the motor 40 in a bearing 42, while it is mounted distally inside the friction gear 50. In this way, axial structural space can be saved, since it is not necessary to provide a second bearing of the output shaft 41 in the motor 40 itself.

The unit composed of motor 40, friction gear 50 and detent 60 can also be produced separately and used in other drives, such that this can be seen as an autonomous solution.

Figure 15:
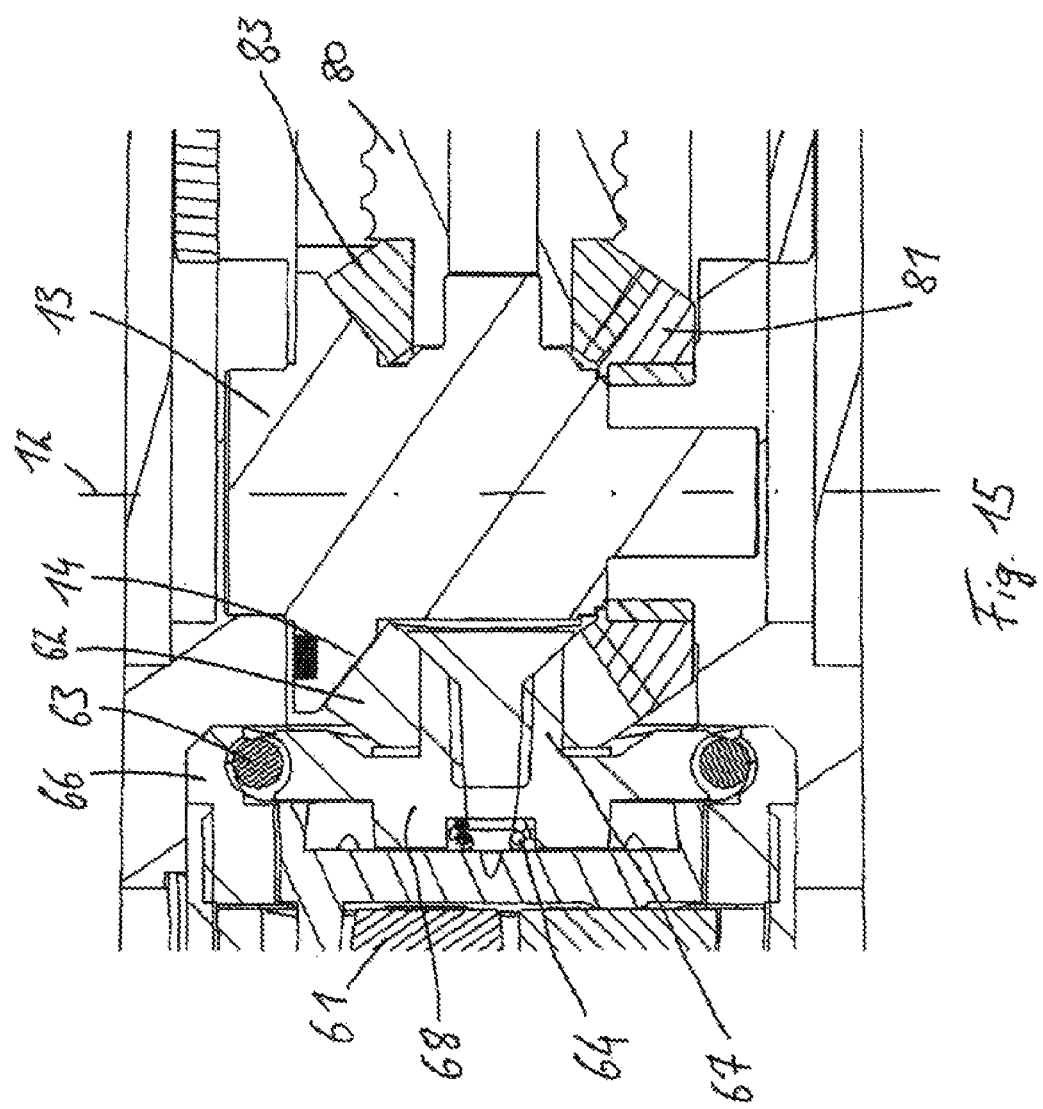
FIG. 15 shows a detailed view of a bevel gear.

FIG. 15 shows, in a sectional view, the gear arrangement and the force transmission from the detent 60 via the output bevel wheel 62 to the recirculating ball spindle 80. A coupling bevel wheel 81 is mounted about the rotation axis 12 of the medial member 20. It is arranged to rotate about a pin 13. The pin 13 has a support surface 14 for the output bevel wheel 62 but does not engage therewith. The rotatable coupling bevel wheel 81 is mounted on the side opposite the support surface 14 and engages in the drive bevel wheel 83, which is connected in a rotationally fixed manner to the spindle 80. In order to achieve a certain degree of axial mobility, the bevel wheel 83 can be mounted in a rotationally fixed and longitudinally displaceable manner on the spindle 80. By means of the arrangement of the coupling toothed wheel 81 about the rotation axis 12, a uniform force transmission can take place independently of the angular position of the medial member 20.

Figure 16:
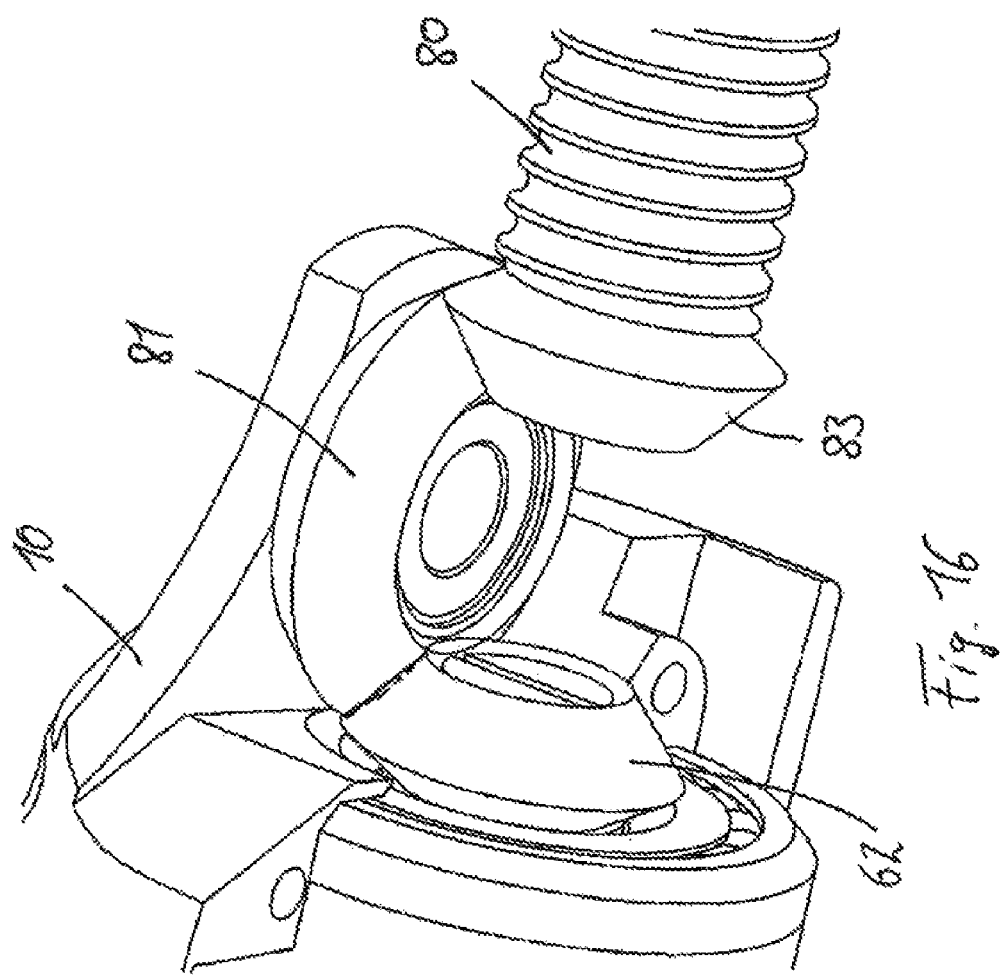
FIG. 16 shows a perspective view of FIG. 15.

FIG. 16 shows a perspective partial sectional view with the output bevel wheel 62, the coupling bevel wheel 81 and the drive bevel wheel 83.

Figure 17:
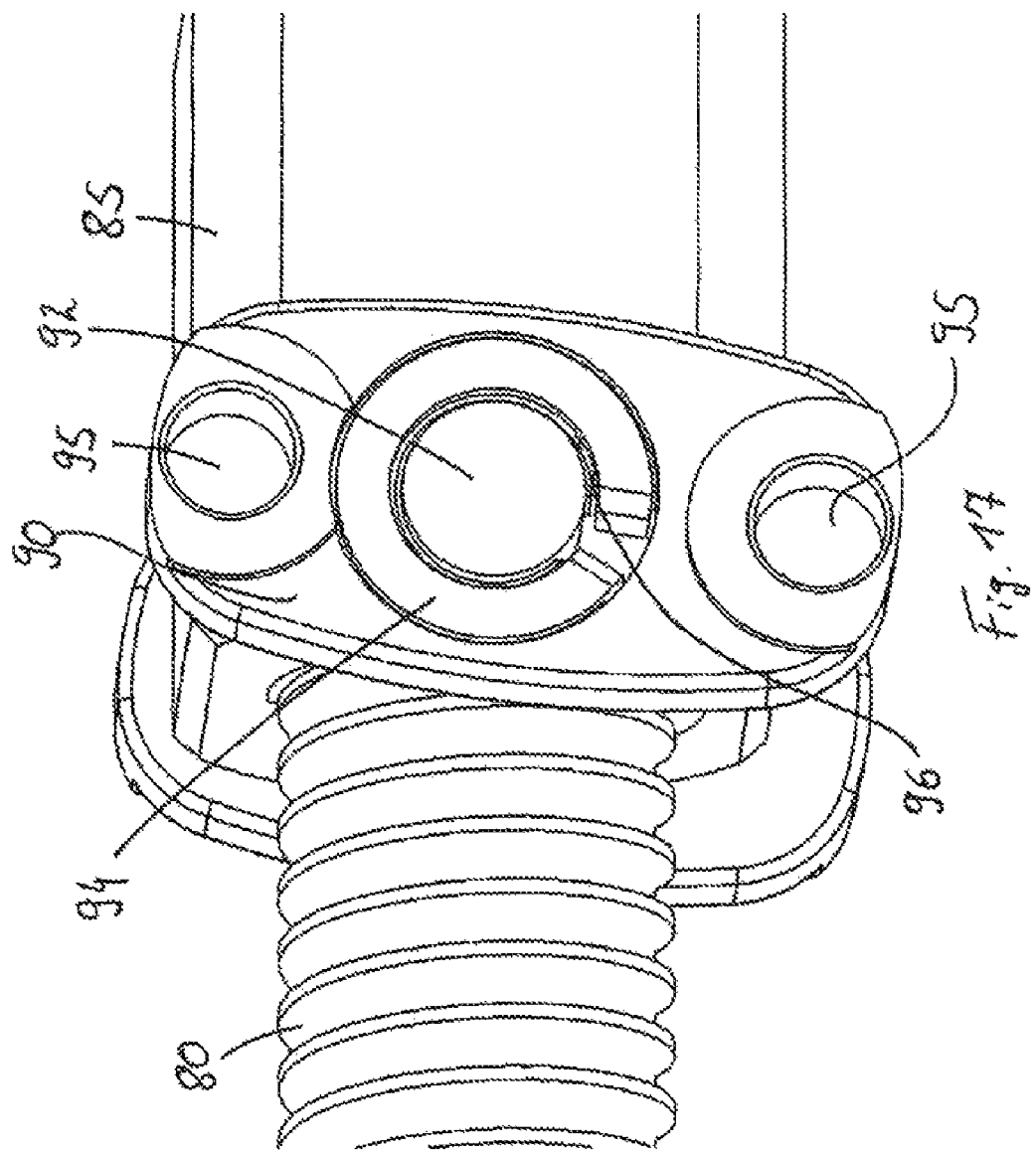
FIG. 17 shows a detailed view of a spindle with spindle nut and balance arm.

FIG. 17 shows a detailed view of the spindle nut 85 on the spindle 80. The balance arm 90 is mounted on the spindle nut 85 on a pin 92. On the pin 92 there is a nose 96 via which the spring 94 is supported, such that the balance arm 90 is located in the illustrated normal position via the spring pretensioning. Because of the clearance between the spring ends, a limited pivoting movement in the counterclockwise direction can take place. To synchronize the movements and coordinate the orientation of the balance arms 90 arranged on both sides of the spindle 80 on the spindle nut 85, these can also be interconnected via a coupling element, such that a bridge or a frame is formed. On the outer ends of the balance arm 90 there are round recesses 95 for receiving pins 97 of the levers 91, 93, as is shown in FIG. 19.

Figure 18:
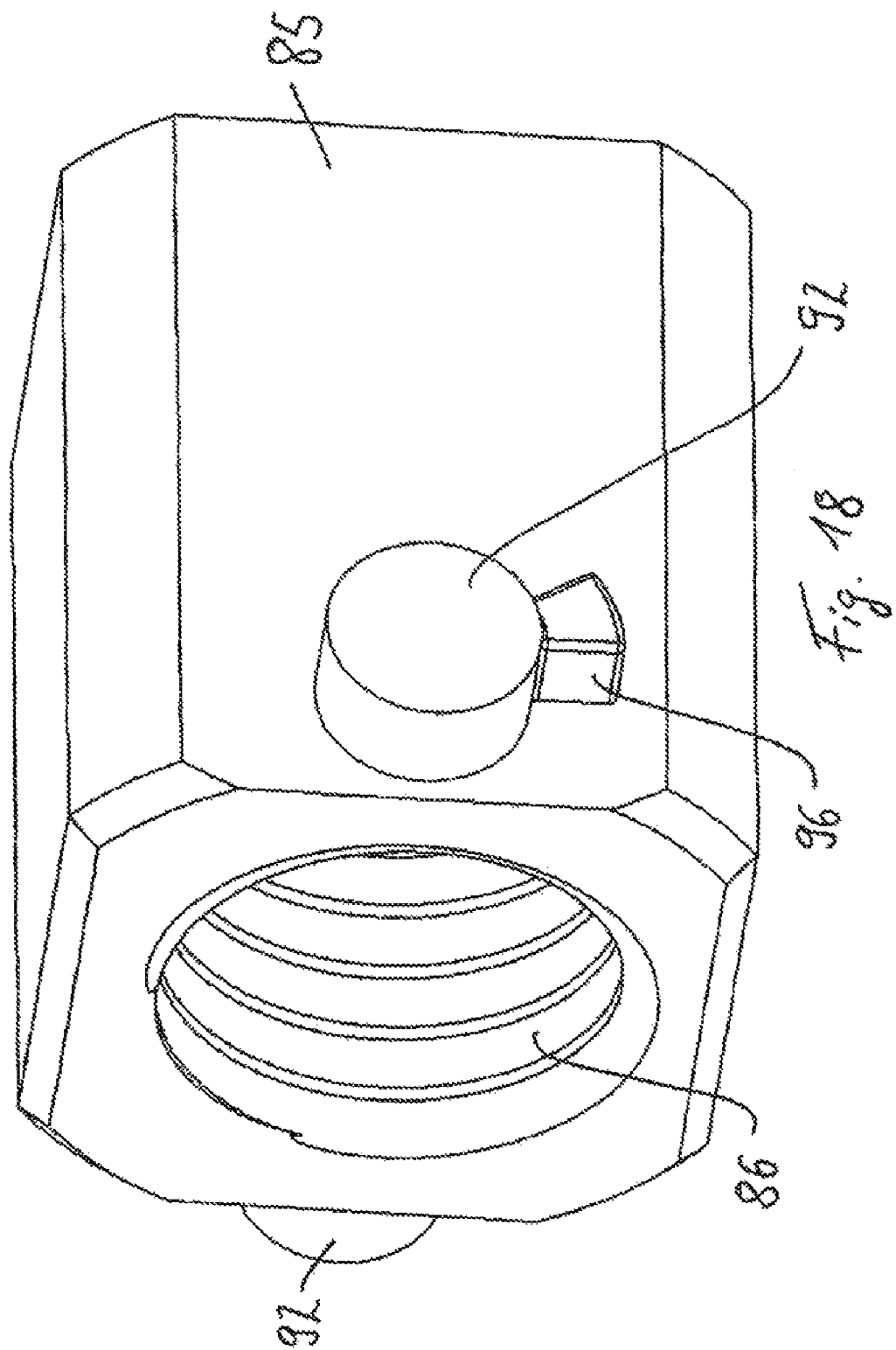
FIG. 18 shows a spindle nut on its own.

FIG. 18 shows a view of the spindle nut 85 on its own, designed as a recirculating ball spindle. Ball tracks 86 are formed in the bore of the spindle nut 85. The pins 92 protrude from both sides, perpendicular to the direction of movement of the spindle nut 85, and comprise the noses 96.

Figure 19:
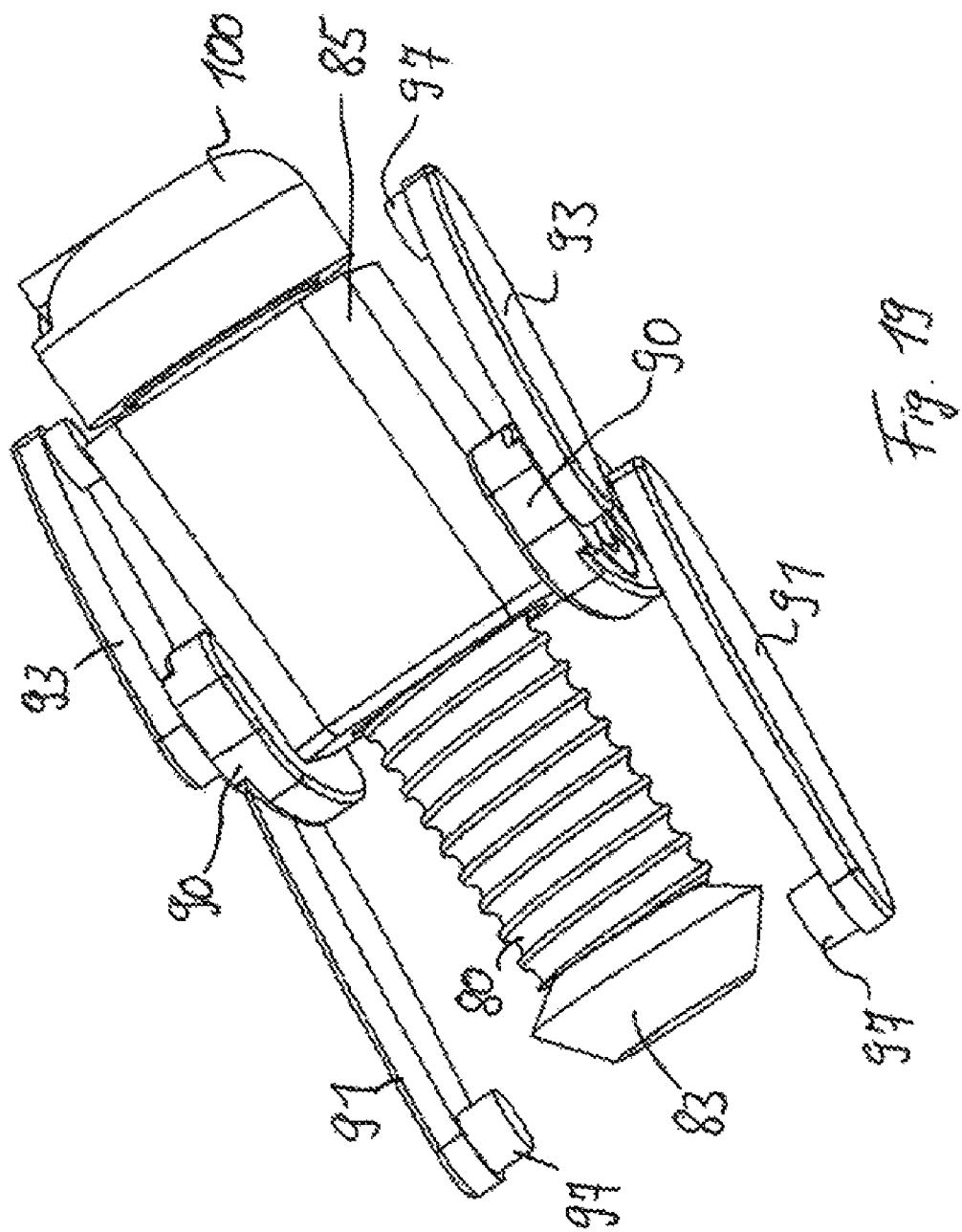
FIG. 19 shows a plan view of an adjusting mechanism.

FIG. 19 shows a plan view of the balance arm lever kinematics. It clearly depicts the balance arms 90 arranged on both sides of the spindle nut 85, and also the symmetrically arranged levers 91, 93 for connecting the balance arms 90 to the adjoining distal and proximal members 30, 10. The bearing and blocking mechanism 100 is shown at the distal end of the spindle 80, and the drive bevel wheel 83 at the proximal end.

Figure 20:
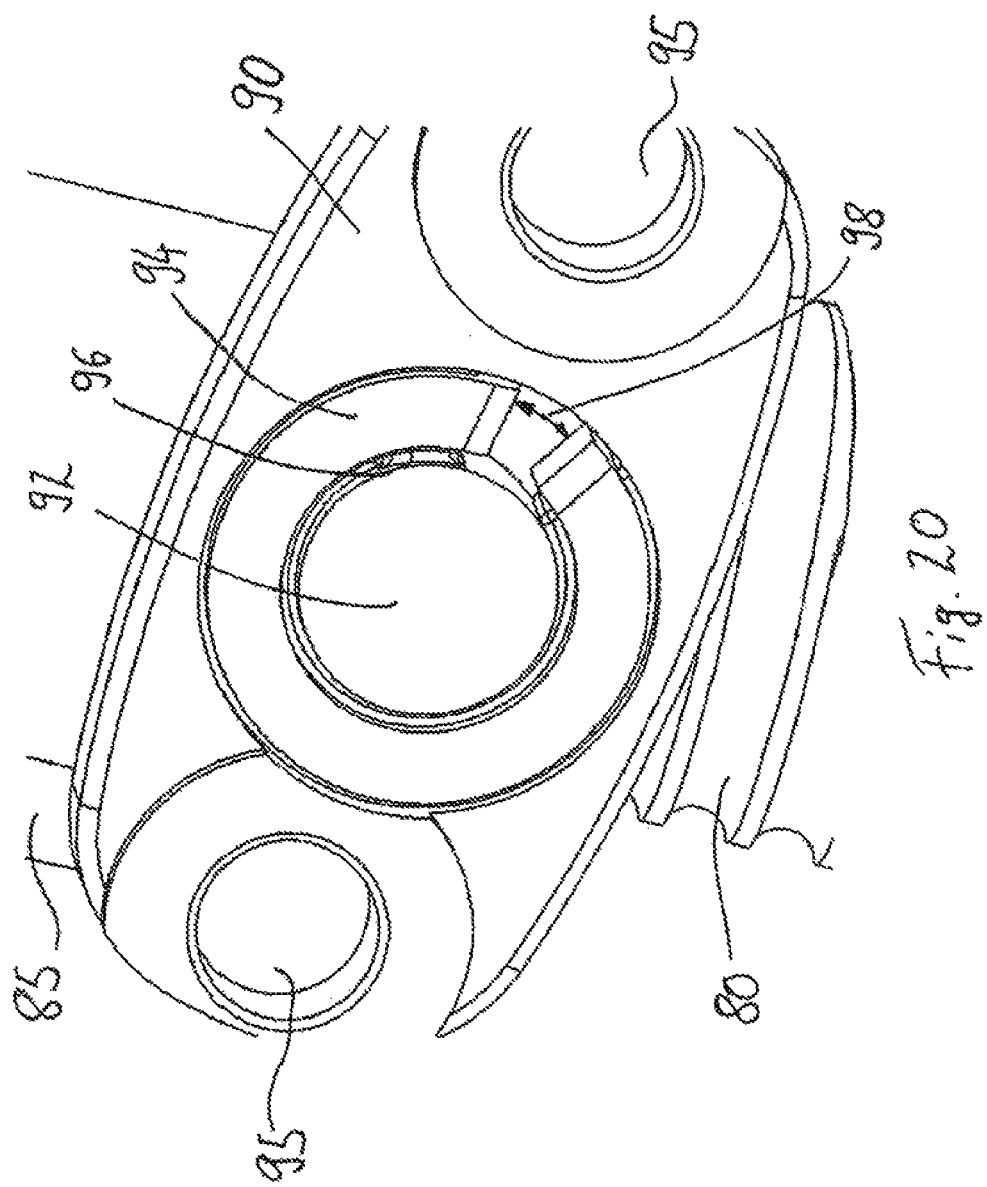
FIG. 20 shows a detailed view of the bearing of a balance arm on the spindle nut.

FIG. 20 shows in detail the movable bearing of the balance arm 90 on the spindle nut 85. The balance arm 90 is arranged about the pin 92 with the nose 96. A pivot area 98 is left free and thus allows the balance arm 90 to turn counterclockwise. The spring 94 serves to keep the balance arm 90 at the correct angle relative to the longitudinal extent of the spindle 80 during the flexion of the prosthetic finger 1. In the event of non-uniform contact of the medial and distal members 20, 30 with an object, the angle can be changed such that a differential action and simple tracking of the member later coming into contact can take place. In contrast to what is shown, the annular spring 94 can also be a compression spring, for example composed of an elastic structural part or a plastic. A bilateral pivotable bearing of the balance arm 90 is also possible.

FIG. 21 shows an overload protection by means of which very high forces, which act against the distal member 30 in the finger bending direction, are carried off not via the balance arm lever system but instead via the recirculating ball spindle 80 and the medial member housing 29. In this way, the kinematic system is protected from destruction in the case of unanticipated high loads, so-called shock loads. In the case of small loads in the finger winding direction, the recirculating ball spindle 80 does not touch the blocking mechanism 100, and instead a small clearance is provided between a shoulder 82 formed on the spindle 80 and a corresponding friction face 180 of the blocking mechanism 100. The balls 101 permit easy rotation in normal operation of the drive and form the distal bearing of the spindle 80. When a force is introduced via the distal member 30, the spindle nut 85 is displaced longitudinally, as a result of which an axial movement of the spindle 80 takes place on account of the lack of self-locking of the recirculating ball spindle gear. In the event of greater loads, the gap between the friction face 180 and the shoulder 82 is therefore overcome by virtue of the elastic configuration of the blocking mechanism, for example as a plastic cap, such that the spindle 80 is braked. As an alternative to a frictional contact, the latter can be a form-fit contact.

FIG. 22 shows a plan view of the medial member 20 with a strain gauge 21 arranged on the top face. Such sensors 21 are needed to measure the inner structural stresses, for example resulting from the loading, so as to provide information to the electronics unit 70. Provision is also made for the prosthetic finger 1 to accommodate further sensors which deliver data concerning the relative position of the members 10, 20, 30 to one another and, if appropriate, to a chassis. These data are conveyed via the conductor 71 to the control unit 70. There, they are evaluated and can then be forwarded via a bus to a central control unit. This significantly reduces the number of lines leading out from the prosthetic fingers 1.

Likewise, a tactile sensor 31 is arranged on the palmar and distal face of the distal member 30 in order to provide haptic information. Gripping forces can also be controlled in this way.

FIG. 23 shows the structure of the prosthetic finger without the housings of the individual finger members 10, 20, 30. The flexible leads 71 are wired in such a way that no buckling is present during operation.

The angle can be measured via a Hall effect sensor which is arranged in all the joints.

All the housings and supports of the individual members can be designed in two pieces in order to permit assembly to the respective attachment members.

The invention claimed is:

1. A prosthetic finger, comprising:
   a proximal member;
   a medial member;
   a distal member, wherein said proximal member, said medial member, and said distal member are mounted pivotably on one another;
   a motor arranged in the prosthetic finger;
   a gear mechanism, wherein said motor is configured to operate with said gear mechanism to rotate the medial member relative to the proximal member;
   a longitudinally movable balance arm in the medial member; and
   levers, wherein said longitudinally movable balance arm is connected via said levers to the proximal member and to the distal member.

2. The prosthetic finger as claimed in claim 1, wherein the longitudinally movable balance arm is mounted on a spindle nut.

3. The prosthetic finger as claimed in claim 1, further comprising a spindle and a spindle nut, wherein the motor is coupled to the spindle which is mounted movably in rotation in the medial member and on which the spindle nut is arranged in a longitudinally displaceable and rotationally fixed manner.

4. The prosthetic finger as claimed in claim 3, wherein the spindle is designed as a recirculating ball spindle.

5. The prosthetic finger as claimed in claim 2 wherein the levers are each formed from two lever members symmetrically arranged on both sides of the spindle nut.

6. The prosthetic finger as claimed in claim 3, wherein the motor and the spindle are coupled to each other via a bevel gear.

7. The prosthetic finger as claimed in claim 6, wherein the bevel gear includes a coupling bevel wheel mounted about a rotation axis of the medial member on either the proximal member or the medial member.

8. The prosthetic finger as claimed in claim 1, wherein the longitudinally movable balance arm is comprised of two balance arms arranged on both sides of an axis of movement in the medial member.

9. The prosthetic finger as claimed in claim 8, wherein the two balance arms are coupled to each other.

10. The prosthetic finger as claimed in claim 1, wherein the longitudinally movable balance arm is fixed at a fixed angle relative to a direction of longitudinal movement.

11. The prosthetic finger as claimed in claim 1, wherein the longitudinally movable balance arm is pivotable from a fixed angle relative to a direction of longitudinal movement.

12. The prosthetic finger as claimed in claim 11, wherein the longitudinally movable balance arm is held in a normal position at said fixed angle by spring pretensioning.

13. The prosthetic finger as claimed in claim 12, wherein the spring pretensioning is generated by a spring element that has a linear or nonlinear ratio between rotation angle and restoring movement.

14. The prosthetic finger as claimed in claim 11, wherein the longitudinally movable balance arm is pivotable in both directions of pivoting.

15. The prosthetic finger as claimed in claim 3, further comprising a blocking mechanism, and wherein said spindle (80) is mounted so as to be axially movable and said blocking mechanism engages with the spindle when a fixed displacement path is exceeded.

16. The prosthetic finger as claimed in claim 15, wherein the blocking mechanism is one of a form-fit brake or a friction brake.

17. The prosthetic finger as claimed in claim 15, wherein the blocking mechanism is an elastic recess with friction surfaces of form-fit elements.

18. The prosthetic finger as claimed in claim 15, wherein the blocking mechanism forms a bearing location for the spindle.

19. The prosthetic finger as claimed in claim 18, wherein the spindle is mounted at the bearing location via one of a ball bearing, roller bearing, or slide bearing.

20. The prosthetic finger as claimed in claim 6, wherein the spindle is mounted on the bevel gear so as to be longitudinally displaceable while being fixed in terms of rotation.

21. The prosthetic finger as claimed in claim 1, further comprising sensor devices arranged on each joint of the prosthetic finger, said sensors detect angular position.

22. The prosthetic finger as claimed in claim 1, further comprising one or more sensor devices for detecting loading.

23. The prosthetic finger as claimed in claim 1, further comprising a sensor arranged in the distal member.

24. The prosthetic finger as claimed in claim 1, further comprising a control electronics unit which controls the motor and an evaluation unit, wherein both said control electronics unit and said evaluation unit are arranged in the prosthetic finger.

25. The prosthetic finger as claimed in claim 24, wherein the control electronics unit is arranged in the proximal member below the motor.

26. The prosthetic finger as claimed in claim 24, further comprising a flexible conductor track and sensors, wherein said flexible conductor track connects the control electronics unit to the sensors and/or to the motor.

27. The prosthetic finger as claimed in claim 1, wherein the motor is coupled to a step-down gear.

28. The prosthetic finger as claimed in claim 27, wherein the step-down gear is a one-stage or multi-stage planetary gear.

29. The prosthetic finger as claimed in claim 27, wherein the motor and the step-down gear are configured as a structural unit with a housing.

30. The prosthetic finger as claimed in claim 29 wherein an output shaft extends from the motor mounted at a proximal end of the housing to the step-down gear at a distal end of the housing.

31. The prosthetic finger as claimed in claim 1, further comprising a detent which follows motor that blocks introduction of a load on an output side and conveys a rotation on a drive side.

32. The prosthetic finger as claimed in claim 31, wherein the detent is a clamping roller freewheel that acts in both directions of rotation.

* * * * *